(12) United States Patent
Mussmann et al.

(10) Patent No.: US 11,739,310 B2
(45) Date of Patent: *Aug. 29, 2023

(54) PERFORMANCE-ENHANCED PROTEASE VARIANTS I

(71) Applicant: Henkel AG & Co. KGaA, Duesseldorf (DE)

(72) Inventors: Nina Mussmann, Willich (DE); Susanne Wieland, Dormagen/Zons (DE); Daniela Herbst, Duesseldorf (DE); Inken Prueser, Duesseldorf (DE); Christian Degering, Erkrath (DE); Daria Strauss, Duesseldorf (DE); Thorsten Eggert, Hattingen (DE); Christian Leggewie, Muelheim an der Ruhr (DE); Layla Fernandez, Cologne (DE); Sabine Griemert, Monheim am Rhein (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 295 days.

This patent is subject to a terminal disclaimer.

(21) Appl. No.: 16/644,180

(22) PCT Filed: Sep. 5, 2018

(86) PCT No.: PCT/EP2018/073893
§ 371 (c)(1),
(2) Date: Mar. 4, 2020

(87) PCT Pub. No.: WO2019/048495
PCT Pub. Date: Mar. 14, 2019

(65) Prior Publication Data
US 2021/0163912 A1    Jun. 3, 2021

(30) Foreign Application Priority Data

Sep. 5, 2017  (DE) .................... 10 2017 215 628.7
Jun. 5, 2018  (DE) .................... 10 2018 208 778.4

(51) Int. Cl.
*C12N 9/54* (2006.01)
*C11D 3/386* (2006.01)
*C11D 11/00* (2006.01)

(52) U.S. Cl.
CPC ............ *C12N 9/54* (2013.01); *C11D 3/386* (2013.01); *C11D 11/0017* (2013.01); *C12Y 304/21062* (2013.01)

(58) Field of Classification Search
None
See application file for complete search history.

(56) References Cited

U.S. PATENT DOCUMENTS

| 6,541,235 B1 * | 4/2003 | Bryan | C12Y 304/21062 435/320.1 |
| 11,124,742 B2 * | 9/2021 | Mussmann | C12N 9/54 |
| 2009/0170745 A1 * | 7/2009 | Merkel | A61P 43/00 435/252.32 |
| 2020/0140787 A1 * | 5/2020 | Mussmann | C11D 3/38681 |

FOREIGN PATENT DOCUMENTS

| WO | 2007131656 A1 | 11/2007 | |
| WO | 2009121725 A1 | 10/2009 | |
| WO | 2011036263 A1 | 3/2011 | |
| WO | 2017162429 A1 | 9/2017 | |
| WO | WO-2017162429 A1 * | 9/2017 | ............ C11D 3/386 |
| WO | 2017198488 A1 | 11/2017 | |
| WO | WO-2017198488 A1 * | 11/2017 | ............... C12N 9/54 |

OTHER PUBLICATIONS

Uniprot, Accession No. P00780, 2016, www.uniprot.org. (Year: 2016).*
"Subtilisin Carlsberg; EC=3.4.21.62; Flags: Precursor", UNIPROT, Jul. 21, 1986, 3 pages.
Bryan, "Protein engineering of subtilisin", Biochimica et Biophysica Acta, 2000, pp. 203-222, vol. 1543, Issue 2.
Von Der Osten et al., "Protein engineering of subtilisins to improve stability in detergent formulations", Journal of Biotechnology, 1993, pp. 55-68, vol. 28, Issue 1.
Vojcic et al., "Advances in protease engineering for laundry detergents", New Biotechnology, 2015, pp. 629-634, vol. 32, No. 6.
International search report from parallel PCT Patent Application PCT/EP2018/073893 dated Nov. 8, 2018, 13 pages (for reference purposes only).

* cited by examiner

*Primary Examiner* — Todd M Epstein
(74) *Attorney, Agent, or Firm* — VIERING JENTSCHURA & PARTNER MBB

(57) ABSTRACT

An amino acid sequence may have at least 70% sequence identity to the amino acid sequence identified in SEQ ID No. 1 over its entire length, and (a) an amino acid substitution on the position corresponding to the position 271, and (b1) at least one other amino acid substitution for at least one of the positions corresponding to the positions 18, 61, 92, 99, 137, 149, 156, 159, 162, 166, 172, 192, 199, 217, 265, or combinations thereof; and/or (b2) an amino acid substitution on the position corresponding to the position 9, and another amino acid substitution for at least one position corresponding to the positions 29, 48, 101, 130, 31, 133, 144, 217, 224, 252, or combinations thereof. Such proteases are useful for in washing or cleaning agents.

17 Claims, No Drawings
Specification includes a Sequence Listing.

PERFORMANCE-ENHANCED PROTEASE VARIANTS I

REFERENCE TO A SEQUENCE LISTING SUBMITTED VIA EFS-WEB

The content of the ASCII text file of the sequence listing named "P75334US_sequencelisting_ST25" which is 60 kb in size was created on Sep. 5, 2017 and electronically submitted via EFS-Web herewith. The sequence listing is incorporated herein by reference in its entirety.

CROSS-REFERENCE TO RELATED APPLICATIONS

The present application is a national stage entry according to 35 U.S.C. § 371 of PCT application No.: PCT/EP2018/073893 filed on Sep. 5, 2018; which claims priority to German application No.: 10 2017 215 628.7 filed on Sep. 5, 2017, as well as to German application No.: 10 2018 208 778.4 filed on Jun. 5, 2018; all of which are incorporated herein by reference in their entirety and for all purposes.

TECHNICAL FIELD

Proteases from *Bacillus pumilus* are disclosed, the amino acid sequences of which have been altered to give them better cleaning performance at low temperatures (e.g. between 20° C. and 40° C.), and also relates to the nucleic acids coding therefor and to the production thereof.

BACKGROUND

Proteases are some of the most important enzymes. They are the longest established enzymes for washing and cleaning agents, and are contained in virtually all modern, effective washing and cleaning agents. They aid in the decomposition of protein-containing stains on the item to be cleaned. Of these, in turn, proteases of the subtilisin type (subtilases, subtilopeptidases, EC 3.4.21.62) are particularly important, which are serine proteases due to the catalytically active amino acids. They act as non-specific endopeptidases and hydrolyze any acid amide bonds that are inside peptides or proteins. Their optimum pH is usually in the distinctly alkaline range. The article "Subtilases: Subtilisin-like Proteases" by R. Siezen, pages 75-95 in "Subtilisin enzymes," published by R. Bott and C. Betzel, New York, 1996, gives an overview of this family, for example. Subtilases are, naturally, formed from microorganisms. In particular, the subtilisins formed and secreted by *Bacillus* species are the most significant group of subtilases.

Examples of the subtilisin proteases used in washing and cleaning agents are the subtilisins BPN' and Carlsberg, the protease PB92, the subtilisins 147 and 309, the protease from *Bacillus lentus*, in particular from *Bacillus lentus* DSM 5483, the subtilisin DY and the enzymes thermitase, proteinase K and proteases TW3 and TW7, which belong to the subtilases but no longer to the subtilisins in the narrower sense, and variants of said proteases having an amino acid sequence that has been altered with respect to the starting protease. Proteases are altered in a targeted manner or randomly using methods known from the prior art, and are thus optimized for the use in washing and cleaning agents, for example. This includes point mutagenesis, deletion or insertion mutagenesis, or fusion with other proteins or protein parts. Appropriately optimized variants are therefore known for the majority of proteases known from the prior art.

European patent application EP2016175A1 discloses, for example, a protease from *Bacillus pumilus* intended for washing and cleaning agents. In general, only selected proteases are suitable for use in liquid, surfactant-containing preparations in any case. Many proteases do not exhibit sufficient catalytic performance in such preparations. For the use of proteases in cleaning agents, therefore, a high catalytic activity under conditions as they are during a wash cycle and a high storage stability is particularly desirable.

Consequently, protease and surfactant-containing liquid formulations from the prior art are disadvantageous in that the proteases contained, under standard washing conditions (e.g. in a temperature range of from 20° C. to 40° C.), do not have satisfactory proteolytic activity or are not storage-stable and the formulations therefore do not exhibit optimal cleaning performance on protease-sensitive stains.

SUMMARY

Surprisingly, it has now been found that a protease from *Bacillus pumilus* or a sufficiently similar protease (based on the sequence identity) has the amino acid substitutions at at least one of the positions corresponding to positions 271 and optionally 9, in each case based on the numbering according to SEQ ID NO:1, and optionally at at least one of the positions corresponding to positions 18, 29, 48, 61, 92, 101, 130, 131, 133, 137, 144, 149, 156, 162, 166, 172, 192, 217, 224, 252 or 265, in each case based on the numbering according to SEQ ID NO:1, is improved in terms of proteolytic activity in standard washing conditions compared with the wild-type form and/or reference mutants and is therefore particularly suitable for use in washing or cleaning agents.

The invention therefore relates, in a first aspect, to a protease comprising an amino acid sequence which has at least 70% sequence identity with the amino acid sequence given in SEQ ID NO:1 over its entire length and has, in each case based on the numbering according to SEQ ID NO:1:
  (a) at the position corresponding to position 271, an amino acid substitution, in particular the amino acid substitution 271E; and
  (b1) at at least one of the positions corresponding to positions 18, 61, 92, 99, 137, 149, 156, 159, 162, 166, 172, 192, 199, 217 or 265, at least one further amino acid substitution; and/or
  (b2) at the position corresponding to position 9, an amino acid substitution, in particular selected from 9T, 9H, 9S and 9A, and at at least one position corresponding to positions 29, 48, 101, 130, 131, 133, 144, 217, 224 and 252, in particular 130, 133, 144, 217 and 252, a further amino acid substitution.

In a second aspect, the invention also relates to a protease comprising an amino acid sequence which has at least 70% sequence identity with the amino acid sequence given in SEQ ID NO:1 over its entire length and, based on the numbering according to SEQ ID NO:1, has at least one amino acid substitution at at least one of the positions corresponding to positions 18, 61, 92, 99, 137, 149, 156, 159, 162, 172, 192, 199, 217 or 265.

In a further aspect, the present invention relates to a protease having an amino acid sequence which has at least 70% sequence identity with the amino acid sequence given in SEQ ID NO:1 over its entire length and which comprises at least one amino acid substitution selected from the group consisting of G131N, T133K, T133Y, N144L or N252S, in each case based on the numbering according to SEQ ID NO:1. In such an embodiment, the protease has either no substitutions at positions 9 and 271, and optionally also no substitution at position 216, or it has a substitution at one of positions 9 and 271, and optionally also a substitution at position 216.

The invention also relates to a method for preparing a protease, as defined above, comprising the substitution of amino acids in a starting protease which has at least 70% sequence identity with the amino acid sequence given in SEQ ID NO:1 over its entire length (a) at the position corresponding to position 271 in SEQ ID NO:1, such that the protease comprises an amino acid substitution, in particular the amino acid substitution 271E, at the position, and (b1) at at least one of the positions corresponding to positions 18, 61, 92, 99, 137, 149, 156, 159, 162, 166, 172, 192, 199, 217 or 265, such that the protease comprises at least one further amino acid substitution, and/or (b2) at the position corresponding to position 9 in SEQ ID NO:1, such that the protease comprises the amino acid substitutions 9T, 9H, 9S or 9A, in particular 9T, at the positions, and at at least one position corresponding to position 29, 48, 101, 130, 131, 133, 144, 224 or 252 in SEQ ID NO:1, such that the protease comprises at least one of the amino acid substitutions 29G, 48V, 101E, 130D, 130S, 130H, 131D, 131N, 131S, 131K, 133K, 133R, 133Y, 144K, 144L, 144A, 224A, 224T, 252T or 252S. The protease that can be obtained by this method has at least 70% sequence identity with the amino acid sequence given in SEQ ID NO:1 over its entire length.

DETAILED DESCRIPTION

A protease within the meaning of the present patent application therefore comprises both the protease as such and a protease prepared by a method. All statements regarding the protease therefore relate both to the protease as such and to the proteases prepared by means of corresponding methods. The proteases described herein have the features (a) and either (b1) or (b2) or (a), (b1) and (b2).

Further aspects relate to the nucleic acids coding for these proteases, to non-human host cells containing proteases or nucleic, and to agents comprising proteases, in particular washing and cleaning agents, to washing and cleaning methods, and to uses of the proteases in washing or cleaning agents in order to remove protein-containing stains.

"At least one," as used herein, means one or more, i.e. 1, 2, 3, 4, 5, 6, 7, 8, 9, 10, 11, 12, 13, 14 or more.

When the protease is defined herein such that it includes "the amino acid substitutions 9T, 9H, 9S or 9A," this means that position 9 is mutated to either T, H, S or A. Therefore, the phrase whereby the protease comprises "the amino acid substitutions 9T, 9H, 9S or 9A and 271E and optionally 216C" means that position 9 is mutated to either T, H, S or A, position 271 is mutated to E and position 216 is optionally mutated to C.

The present invention is based on the surprising finding of the inventors that amino acid substitutions at the positions described herein bring about improved performance of this altered protease (proteolytic activity under standard washing conditions) in washing and cleaning agents. Optionally, improved storage stability of this altered protease can additionally be brought about in washing and cleaning agents. This is particularly surprising insofar as none of the above-mentioned amino acid substitutions has previously been associated with increased catalytic activity and/or increased storage stability of the protease.

In non-limiting embodiments of the protease, the protease has amino acid substitutions (A) (i) at the positions corresponding to positions 9, 131 and 271, in each case based on the numbering according to SEQ ID NO:1, and (ii) at at least one of the positions corresponding to positions 29, 48, 101, 130, 133, 144, 224 or 252, in each case based on the numbering according to SEQ ID NO:1;

(B) (i) at the positions corresponding to positions 9, 133 and 271, in each case based on the numbering according to SEQ ID NO:1, and (ii) at at least one of the positions corresponding to positions 29, 48, 101, 130, 131, 144, 224 or 252, in each case based on the numbering according to SEQ ID NO:1;

(C) (i) at the positions corresponding to positions 9, 224 and 271, in each case based on the numbering according to SEQ ID NO:1, and (ii) at at least one of the positions corresponding to positions 29, 48, 101, 130, 131, 133, 144 or 252, in each case based on the numbering according to SEQ ID NO:1;

(D) (i) at the positions corresponding to positions 9, 130 and 271, in each case based on the numbering according to SEQ ID NO:1, and (ii) at at least one of the positions corresponding to positions 29, 48, 101, 131, 133, 144, 224 or 252, in each case based on the numbering according to SEQ ID NO:1;

(E) (i) at the positions corresponding to positions 9, 144 and 271, in each case based on the numbering according to SEQ ID NO:1, and (ii) at at least one of the positions corresponding to positions 29, 48, 101, 130, 131, 133, 224 or 252, in each case based on the numbering according to SEQ ID NO:1;

(F) at the positions corresponding to positions 9, 252 and 271, in each case based on the numbering according to SEQ ID NO:1, and (ii) at at least one of the positions corresponding to positions 29, 48, 101, 130, 131, 133, 144 or 224, in each case based on the numbering according to SEQ ID NO:1;

(G) (i) at the positions corresponding to positions 9, 130, 133 and 271, in each case based on the numbering according to SEQ ID NO:1, and optionally (ii) at at least one of the positions corresponding to positions 29, 48, 101, 131, 144, 224 or 252, in each case based on the numbering according to SEQ ID NO:1;

(H) (i) at the positions corresponding to positions 9, 130, 144 and 271, in each case based on the numbering according to SEQ ID NO:1, and optionally (ii) at at least one of the positions corresponding to positions 29, 48, 101, 131, 133, 224 or 252, in each case based on the numbering according to SEQ ID NO:1;

(I) (i) at the positions corresponding to positions 9, 130, 252 and 271, in each case based on the numbering according to SEQ ID NO:1, and optionally (ii) at at least one of the positions corresponding to positions 29, 48, 101, 131, 133, 144 or 224, in each case based on the numbering according to SEQ ID NO:1;

(J) (i) at the positions corresponding to positions 9, 133, 144 and 271, in each case based on the numbering according to SEQ ID NO:1, and optionally (ii) at at least one of the positions corresponding to positions 29, 48, 101, 130, 131, 224 or 252, in each case based on the numbering according to SEQ ID NO:1;

(K) (i) at the positions corresponding to positions 9, 133, 252 and 271, in each case based on the numbering according to SEQ ID NO:1, and optionally (ii) at at least one of the positions corresponding to positions 29, 48, 101, 130, 131, 144 or 224, in each case based on the numbering according to SEQ ID NO:1;

(L) at the positions corresponding to positions 9, 144, 252 and 271, in each case based on the numbering according to SEQ ID NO:1, and optionally (ii) at at least one of the positions corresponding to positions 29, 48, 101, 130, 131, 133 or 224, in each case based on the numbering according to SEQ ID NO:1;

(M) at the positions corresponding to positions 9, 130, 144, 252 and 271, in each case based on the numbering according to SEQ ID NO:1, and optionally (ii) at at least one of the positions corresponding to positions 29, 48, 101, 131, 133 or 224, in each case based on the numbering according to SEQ ID NO:1;

(N) at the positions corresponding to positions 9, 133, 144, 252 and 271, in each case based on the numbering according to SEQ ID NO:1, and optionally (ii) at at least one of the positions corresponding to positions 29, 48, 101, 130, 131 or 224, in each case based on the numbering according to SEQ ID NO:1;

(O) at the positions corresponding to positions 9, 130, 133, 252 and 271, in each case based on the numbering according to SEQ ID NO:1, and optionally (ii) at at least one of the positions corresponding to positions 29, 48, 101, 131, 144 or 224, in each case based on the numbering according to SEQ ID NO:1;

(P) at the positions corresponding to positions 9, 130, 133, 144 and 271, in each case based on the numbering according to SEQ ID NO:1, and optionally (ii) at at least one of the positions corresponding to positions 29, 48, 101, 131, 224 or 252, in each case based on the numbering according to SEQ ID NO:1; or (Q) at the positions corresponding to positions 9, 130, 133, 144, 252 and 271, in each case based on the numbering according to SEQ ID NO:1, and optionally (ii) at at least one of the positions corresponding to positions 29, 48, 101, 131 or 224, in each case based on the numbering according to SEQ ID NO:1.

In further embodiments, proteases are those having amino acid substitutions at the positions:

9 and 271 and at least one of 131, 133, 224, 130 and 144, and optionally at least one of 29, 48, 101 and 252;

9+271+131+224 and optionally at least one of 29, 48, 101, 130, 133, 144 or 252;

9+271+131+133 and optionally at least one of 29, 48, 101, 130, 144, 224 or 252;

9+271+131+133+224 and optionally at least one of 29, 48, 101, 130, 144 or 252; or 9+271+131+133+224+130 and optionally at least one of 29, 48, 101, 144 or 252;

In various embodiments, the protease has (1) at the position corresponding to position 271, an amino acid substitution, in particular the amino acid substitution 271E; and (2-1) at the positions corresponding to positions 9, 130, 144 and 252, the amino acid substitutions 9T, 130D, 144K and 252T; and/or (2-2) at one or more of the positions corresponding to positions 18, 61, 92, 99, 137, 149, 156, 159, 162, 166, 172, 192, 199, 217 or 265, one or more amino acid substitutions selected from: 18D, 61Y, 92S, 99Y, 137K, 149I, 156G, 156Y, 159I, 162S, 166M, 172G, 172P, 192V, 199M, 217M and 265A.

Here, feature (1) can be combined with feature (2-1), feature (2-2), or both.

In different embodiments, the protease has an amino acid substitution, in particular the amino acid substitution 271E, at the position corresponding to position 271; and has the amino acid substitutions 9T, 130D, 144K and 252T at the positions corresponding to positions 9, 130, 144 and 252; and optionally has at least one, for example 1, 2, 3, 4, 5, 6, 7, 8, 9, 10, 11, 12 or 13, for example 1, 2, 3 or 4, further amino acid substitution(s) at one or more of the positions corresponding to positions 62, 99, 133, 137, 149, 156, 162, 166, 172, 192, 199, 217, 224 or 265, these being selected from: 62S, 99Y, 133R, 133K, 133A, 137K, 149I, 156G, 156Y, 162S, 166M, 172G, 172P, 192V, 199M, 217M, 224A and 265A. Such proteases are disclosed for example in example 1. Non-limiting embodiments include those proteases which have an amino acid substitution, in particular the amino acid substitution 271E, at the position corresponding to position 271; and have the amino acid substitutions 9T, 130D, 144K and 252T at the positions corresponding to positions 9, 130, 144 and 252; and optionally at least one, for example 1, 2, 3, 4, 5, 6 or 7, for example 1, 2, 3 or 4, further amino acid substitution(s) at one or more of the positions corresponding to positions 62, 133, 137, 162, 192, 217 or 265, these being selected from: 62S, 133R, 133K, 133A, 137K, 162S, 192V, 217M and 224A.

In further embodiments, the protease has amino acid substitutions at the following positions (in the numbering according to SEQ ID NO:1):

9+271+29
9+271+48
9+271+101
9+271+130
9+271+131
9+271+133
9+271+144
9+271+224
9+271+252
9+271+29+48
9+271+29+101
9+271+29+130
9+271+29+131
9+271+29+133
9+271+29+144
9+271+29+224
9+271+29+252
9+271+48+101
9+271+48+130
9+271+48+131
9+271+48+133
9+271+48+144
9+271+48+224
9+271+48+252
9+271+101+130
9+271+101+131
9+271+101+133
9+271+101+144
9+271+101+224
9+271+101+252
9+271+130+131
9+271+130+133
9+271+130+144
9+271+130+224
9+271+130+252
9+271+131+133
9+271+131+144
9+271+131+224
9+271+131+252
9+271+133+144
9+271+133+224
9+271+133+252

9+271+144+224
9+271+144+252
9+271+224+252
9+271+29+48+101
9+271+29+48+130
9+271+29+48+131
9+271+29+48+133
9+271+29+48+144
9+271+29+48+224
9+271+29+48+252
9+271+29+101+130
9+271+29+101+131
9+271+29+101+133
9+271+29+101+144
9+271+29+101+224
9+271+29+101+252
9+271+29+130+131
9+271+29+130+133
9+271+29+130+144
9+271+29+130+224
9+271+29+130+252
9+271+29+131+133
9+271+29+131+144
9+271+29+131+224
9+271+29+131+252
9+271+29+133+144
9+271+29+133+224
9+271+29+133+252
9+271+29+144+224
9+271+29+144+252
9+271+29+224+252
9+271+48+101+130
9+271+48+101+131
9+271+48+101+133
9+271+48+101+144
9+271+48+101+224
9+271+48+101+252
9+271+48+130+131
9+271+48+130+133
9+271+48+130+144
9+271+48+130+224
9+271+48+130+252
9+271+48+131+133
9+271+48+131+144
9+271+48+131+224
9+271+48+131+252
9+271+48+133+144
9+271+48+133+224
9+271+48+133+252
9+271+48+144+224
9+271+48+144+252
9+271+48+224+252
9+271+101+130+131
9+271+101+130+133
9+271+101+130+144
9+271+101+130+224
9+271+101+130+252
9+271+101+131+133
9+271+101+131+144
9+271+101+131+224
9+271+101+131+252
9+271+101+133+144
9+271+101+133+224
9+271+101+133+252
9+271+101+144+224
9+271+101+144+252
9+271+101+224+252
9+271+130+131+133
9+271+130+131+144
9+271+130+131+224
9+271+130+131+252
9+271+130+133+144
9+271+130+133+224
9+271+130+133+252
9+271+130+144+224
9+271+130+144+252
9+271+130+224+252
9+271+131+133+144
9+271+131+133+224
9+271+131+133+252
9+271+131+144+224
9+271+131+144+252
9+271+131+224+252
9+271+133+144+224
9+271+133+144+252
9+271+133+224+252
9+271+144+224+252
9+271+29+48+101+130
9+271+29+48+101+131
9+271+29+48+101+133
9+271+29+48+101+144
9+271+29+48+101+224
9+271+29+48+101+252
9+271+29+48+130+131
9+271+29+48+130+133
9+271+29+48+130+144
9+271+29+48+130+224
9+271+29+48+130+252
9+271+29+48+131+133
9+271+29+48+131+144
9+271+29+48+131+224
9+271+29+48+131+252
9+271+29+48+133+144
9+271+29+48+133+224
9+271+29+48+133+252
9+271+29+101+130+131
9+271+29+101+130+133
9+271+29+101+130+144
9+271+29+101+130+224
9+271+29+101+130+252
9+271+29+101+131+133
9+271+29+101+131+144
9+271+29+101+131+224
9+271+29+101+131+252
9+271+29+101+133+144
9+271+29+101+133+224
9+271+29+101+133+252
9+271+29+101+144+224
9+271+29+101+144+252
9+271+29+101+224+252
9+271+29+130+131+133
9+271+29+130+131+144
9+271+29+130+131+224
9+271+29+130+131+252
9+271+29+130+133+144
9+271+29+130+133+224
9+271+29+130+133+252
9+271+29+130+144+224
9+271+29+130+144+252
9+271+29+130+224+252
9+271+29+131+133+144
9+271+29+131+133+224
9+271+29+131+133+252
9+271+29+131+144+224

9+271+29+131+144+252
9+271+29+131+224+252
9+271+29+133+144+224
9+271+29+133+144+252
9+271+29+133+224+252
9+271+29+144+224+252
9+271+48+101+130+131
9+271+48+101+130+133
9+271+48+101+130+144
9+271+48+101+130+224
9+271+48+101+130+252
9+271+48+101+131+133
9+271+48+101+131+144
9+271+48+101+131+224
9+271+48+101+131+252
9+271+48+101+133+144
9+271+48+101+133+224
9+271+48+101+133+252
9+271+48+101+144+224
9+271+48+101+144+252
9+271+48+101+224+252
9+271+48+130+131+133
9+271+48+130+131+144
9+271+48+130+131+224
9+271+48+130+131+252
9+271+48+130+133+144
9+271+48+130+133+224
9+271+48+130+133+252
9+271+48+130+144+224
9+271+48+130+144+252
9+271+48+130+224+252
9+271+48+131+133+144
9+271+48+131+133+224
9+271+48+131+133+252
9+271+48+131+144+224
9+271+48+131+144+252
9+271+48+131+224+252
9+271+48+133+144+224
9+271+48+133+144+252
9+271+48+133+224+252
9+271+48+144+224+252
9+271+101+130+131+133
9+271+101+130+131+144
9+271+101+130+131+224
9+271+101+130+131+252
9+271+101+130+133+144
9+271+101+130+133+224
9+271+101+130+133+252
9+271+101+130+144+224
9+271+101+130+144+252
9+271+101+130+224+252
9+271+101+131+133+144
9+271+101+131+133+224
9+271+101+131+133+252
9+271+101+131+144+224
9+271+101+131+144+252
9+271+101+131+224+252
9+271+101+133+144+224
9+271+101+133+144+252
9+271+101+133+224+252
9+271+101+144+224+252
9+271+130+131+133+144
9+271+130+131+133+224
9+271+130+131+133+252
9+271+130+131+144+224
9+271+130+131+144+252
9+271+130+131+224+252
9+271+130+133+144+224
9+271+130+133+144+252
9+271+130+133+224+252
9+271+130+144+224+252
9+271+131+133+144+224
9+271+131+133+144+252
9+271+131+133+224+252
9+271+131+144+224+252
9+271+133+144+224+252

In various embodiments, the aforementioned variants do not have further substitutions or have only one or more additional substitutions in the positions from the group of positions of 29, 48, 101, 130, 131, 133, 144, 224 and 252, if these have not yet been mentioned above. In further embodiments, in particular in all the embodiments described above, the protease has an additional amino acid substitution at the position corresponding to position 217, based on the numbering according to SEQ ID NO:1. This amino acid substitution may be the amino acid substitution 217M.

Further embodiments relate to protease variants which have amino acid substitutions at the following positions (in the numbering according to SEQ ID NO:1):

271+18
271+61
271+92
271+99
271+137
271+149
271+156
271+159
271+162
271+166
271+172
271+192
271+199
271+217
271+265
271+18+61
271+18+92
271+18+99
271+18+137
271+18+149
271+18+156
271+18+159
271+18+162
271+18+166
271+18+172
271+18+192
271+18+199
271+18+217
271+18+265
271+61+92
271+61+99
271+61+137
271+61+149
271+61+156
271+61+159
271+61+162
271+61+166
271+61+172
271+61+192
271+61+199
271+61+217
271+61+265
271+92+99
271+92+137
271+92+149

271+92+156
271+92+159
271+92+162
271+92+166
271+92+172
271+92+192
271+92+199
271+92+217
271+92+265
271+99+137
271+99+149
271+99+156
271+99+159
271+99+162
271+99+166
271+99+172
271+99+192
271+99+199
271+99+217
271+99+265
271+137+149
271+137+156
271+137+159
271+137+162
271+137+166
271+137+172
271+137+192
271+137+199
271+137+217
271+137+265
271+149+156
271+149+159
271+149+162
271+149+166
271+149+172
271+149+192
271+149+199
271+149+217
271+149+265
271+156+159
271+156+162
271+156+166
271+156+172
271+156+192
271+156+199
271+156+217
271+156+265
271+159+162
271+159+166
271+159+172
271+159+192
271+159+199
271+159+217
271+159+265
271+162+166
271+162+172
271+162+192
271+162+199
271+162+217
271+162+265
271+166+172
271+166+192
271+166+199
271+166+217
271+166+265
271+172+192
271+172+199
271+172+217
271+172+265
271+192+199
271+192+217
271+192+265
271+199+217
271+199+265
271+217+265

In various embodiments, the aforementioned variants do not have further substitutions or have only one or more additional substitutions in the positions from the group of positions of 18, 61, 92, 99, 137, 149, 156, 159, 162, 166, 172, 192, 199, 217 and 265, if these have not yet been mentioned above.

In all the aforementioned variants, the corresponding exchanges are in particular those mentioned above, i.e. 9T, 9H, 9S, 9A, 29G, 48V, 101E, 130D, 130S, 130H, 131D, 131N, 131S, 131K, 133K, 133R, 133Y, 144K, 144L, 144A, 224A, 224T, 252S, 252T and/or 271E. 9T, 130D, 133R/K, 144K, 252T/S and/or 271E. Accordingly, in particular the above-mentioned variants in which the aforementioned substitutions occur are preferred. A variant which has the substitutions 9T, 130D, 144K, 252T and 271E, and optionally also 133R/K and/or 217M may be included in a non-limiting embodiment.

In embodiments of the protease, i.e. in particular the variants listed above, the protease has amino acid substitutions at the positions corresponding to positions 18, 61, 92, 99, 137, 149, 156, 159, 162, 166, 172, 192, 199, 217 or 265, which amino acid substitutions are selected from: 18D, 61Y, 92S, 99Y, 137K, 149I, 156G, 156Y, 159I, 162S, 166M, 172G, 172P, 192V, 199M, 217M and 265A.

In further embodiments, in particular in all the embodiments described above, the protease has an additional amino acid substitution at the position corresponding to position 216, based on the numbering according to SEQ ID NO:1. This amino acid substitution may be the amino acid substitution S216C. In various embodiments, however, the application described herein also relates to protease variants which do not have the substitution 216C, in particular do not have a substitution in the position 216 in the numbering according to SEQ ID NO:1.

In various embodiments, the protease contains at least one amino acid substitution selected from the group consisting of A29G, A48V, D101E, N130D, N130S, N130H, G131D, G131N, G131S, G131K, T133K, T133R, T133Y, N144K, N144L, N144A, S224A, S224T or N252S, in each case based on the numbering according to SEQ ID NO:1. In yet further embodiments, the protease contains the amino acid substitutions (1) P9T, P9H, P9S or P9A and (2) Q271E and optionally also (3) S216C and additionally one of the following amino acid substitution variants: (I) A48V, G131S, T133R and S224A; (II) G131D, T133R and S224A; (III) N130D, G131N, T133K and N144K; (IV) A29G, N130D, G131N and T133R; (V) N130D, G131S, T133K and S224A; (VI) N130D, G131N, T133K, N144L and N252S; (VII) G131S, N144K and S224T; (VIII) N130S, G131S, T133Y, N144L and S224A; (IX) D101E, G131N and S224A; or (X) N130H, G131S and S224A, the numbering being based in each case on the numbering according to SEQ ID NO:1.

In various embodiments, the proteases have an amino acid sequence according to one of SEQ ID Nos. 3-12, 16-25 or 15-25.

The proteases typically have improved cleaning performance, i.e. increased catalytic activity in washing or cleaning agents. In various embodiments, the proteases may have a proteolytic activity which, based on the wild type (SEQ ID NO:1), is at least 101%, such as at least 102% or more. In various embodiments, the proteases have a proteolytic activity which, based on a reference mutation variant of the protease (SEQ ID NO:13 and/or SEQ ID NO:2 and/or SEQ ID NO:14), is at least 110%, at least 115%, at least 120%, at least 125%, at least 130%, at least 135%, at least 140%, at least 145%, at least 150%, at least 155% or at least 160%. Such performance-enhanced proteases allow improved washing results on proteolytically sensitive stains in various temperature ranges, in particular in a temperature range of from 20° C. to 40° C.

Independently of or in addition to increased cleaning performance, the proteases may also have increased storage stability in washing or cleaning agents. This means that they have increased stability in washing or cleaning agents in comparison with the wild-type enzyme and in particular in contrast to the initial variant or a reference mutation variant of the protease (SEQ ID NO:2, 13 or 14), in particular when stored for 3 or more days, 4 or more days, 7 or more days, 10 or more days, 12 or more days, 14 or more days, 21 or more days or 28 or more days.

The proteases exhibit enzymatic activity, i.e. they are capable of hydrolyzing peptides and proteins, in particular in a washing or cleaning agent. A protease is therefore an enzyme which catalyzes the hydrolysis of amide/peptide bonds in protein/peptide substrates and is thus able to cleave proteins or peptides. Furthermore, a protease is a mature protease, i.e. the catalytically active molecule without signal peptide(s) and/or propeptide(s). Unless stated otherwise, the sequences given also each refer to mature (processed) enzymes.

In various embodiments, the protease is a free enzyme. This means that the protease can act directly with all the components of an agent and, if the agent is a liquid agent, that the protease is in direct contact with the solvent of the agent (e.g. water). In other embodiments, an agent may contain proteases that form an interaction complex with other molecules or that contain a "coating." In this case, an individual protease molecule or multiple protease molecules may be separated from the other components of the agent by a surrounding structure. Such a separating structure may arise from, but is not limited to, vesicles such as a micelle or a liposome. The surrounding structure may also be a virus particle, a bacterial cell or a eukaryotic cell. In various embodiments, an agent may include cells of *Bacillus pumilus* or *Bacillus subtilis* which express the proteases, or cell culture supernatants of such cells.

In various embodiments, the protease comprises an amino acid sequence which, over its entire length, is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence given in SEQ ID NO:1, and has the amino acid substitutions given above in each case based on the numbering according to SEQ ID NO:1. In the context of various embodiments, the feature whereby a protease has the given substitutions means that it contains one (of the given) substitution(s) at the relevant position, i.e. at least the given positions are not otherwise mutated or deleted, for example by fragmenting of the protease. The amino acid sequences of exemplary proteases which are detected are given in SEQ ID Nos: 3-12 and 16-25 or 17-25. In various embodiments, the proteases described herein, with the exception of the explicitly mentioned substitutions, have the sequence of SEQ ID NO:1, i.e. apart from the substituted positions, they are 100% identical to the sequence according to SEQ ID NO: 1.

The identity of nucleic acid or amino acid sequences is determined by a sequence comparison. This sequence comparison is based on the BLAST algorithm established and commonly used in the prior art (cf. for example Altschul et al. (1990): "Basic local alignment search tool," J. Mol. Biol. 215:403-410, and Altschul et al. (1997): "Gapped BLAST and PSI-BLAST: a new generation of protein database search programs," Nucleic Acids Res. 25:3389-3402) and in principle occurs by associating similar sequences of nucleotides or amino acids in the nucleic acid or amino acid sequences. A tabular association of the positions concerned is referred to as alignment. Another algorithm which is available in the prior art is the FASTA algorithm. Sequence comparisons (alignments), in particular multiple sequence comparisons, are created using computer programs. The Clustal series (cf. for example, Chenna et al. (2003): "Multiple sequence alignment with the Clustal series of programs," Nucleic Acid Res. 31:3497-3500), T-Coffee (cf. for example, Notredame et al. (2000): "T-Coffee: A novel method for multiple sequence alignments," J. Mol. Biol. 302:205-217) or programs based on these programs or algorithms are frequently used, for example. Sequence comparisons (alignments) using the computer program Vector NTI® Suite 10.3 (Invitrogen Corporation, 1600 Faraday Avenue, Carlsbad, Calif., USA) with the predetermined, default parameters, and the AlignX module of which for sequence comparisons is based on ClustalW, are also possible. Unless stated otherwise, the sequence identity given herein is determined by the BLAST algorithm.

Such a comparison also allows a statement regarding the similarity of the compared sequences. It is usually given in percent identity, i.e. the proportion of identical nucleotides or amino acid residues in said sequences, or corresponding positions in an alignment. The broader concept of homology takes conserved amino acid substitutions into account in the case of amino acid sequences, i.e. amino acids having similar chemical activity, since they usually perform similar chemical activities within the protein. Therefore, the similarity of the compared sequences may also be stated as percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often have identical functions. They can be small and comprise only a few nucleotides or amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular nucleic acid or amino acid sequence indicated.

In the context of various embodiments, the indication that an amino acid position corresponds to a numerically designated position in SEQ ID NO:1 therefore means that the corresponding position is associated with the numerically designated position in SEQ ID NO:1 in an alignment as defined above.

In a further embodiment, the protease is characterized in that the cleaning performance thereof is not significantly reduced compared with that of a protease comprising an amino acid sequence that corresponds to the amino acid sequence given in SEQ ID NO:13 and/or SEQ ID NO:2 and/or SEQ ID NO:14, i.e. has at least 80% of the reference washing performance, such as at least 100%, or at least 110% or more. The cleaning performance can be determined in a washing system containing a washing agent in a dosage between 4.5 and 7.0 grams per liter of washing liquor, and the protease, the proteases to be compared being used in the same concentration (based on active protein) and the cleaning performance with respect to a stain on cotton being determined by measuring the degree of cleaning of the washed textiles.

For example, the washing process can take place for 60 minutes at a temperature of 40° C. and the water can have a water hardness between 15.5 and 16.5° (German hardness). The concentration of the protease in the washing agent intended for this washing system is 0.001 to 0.1 wt. %, such as 0.01 to 0.06 wt. % based on active, purified protein.

A liquid reference washing agent for such a washing system may be composed as follows (all figures in wt. %): 4.4% alkyl benzene sulfonic acid, 5.6% further anionic surfactants, 2.4% $C_{12}$-$C_{18}$ Na salts of fatty acids (soaps), 4.4% non-ionic surfactants, 0.2% phosphonates, 1.4% citric acid, 0.95% NaOH, 0.01% defoamer, 2% glycerol, 0.08% preservatives, 1% ethanol, and the remainder being demineralized water. In a non-limiting embodiment, the dosage of the liquid washing agent is between 4.5 and 6.0 grams per liter of washing liquor, for example 4.7, 4.9 or 5.9 grams per liter of washing liquor. Washing in a pH range between pH 7 and pH 10.5, such as between pH 7.5 and pH 8.5, is suitable.

In the context of various embodiments, the cleaning performance is determined for example at 20° C. or 40° C. using a liquid washing agent as stated above, the washing process being carried out for 60 minutes at 600 rpm.

The degree of whiteness, i.e. the lightening of stains, as a measure of the cleaning performance is determined by optical measuring methods, such as photometrically. A suitable device for this purpose is for example the Minolta CM508d spectrometer. Usually, the devices used for the measurement are calibrated beforehand with a white standard, such as a supplied white standard.

The activity-equivalent use of the respective protease ensures that the respective enzymatic properties, for example the cleaning performance on certain stains, are compared even if the ratio of active substance to total protein (the values of the specific activity) significantly differs. In general, a low specific activity can be compensated for by adding a larger amount of protein.

Otherwise, methods for determining protease activity are well known to, and routinely used by, a person skilled in the art of enzyme technology. For example, such methods are disclosed in Tenside, vol. 7 (1970), pp. 125-132. Alternatively, the protease activity can be determined by the release of the chromophore para-nitroaniline (pNA) from the substrate suc-L-Ala-L-Ala-L-Pro-L-Phe-p-nitroanilide (AAPF). The protease cleaves the substrate and releases pNA. The release of the pNA causes an increase in absorbance at 410 nm, the temporal progression of which is a measure of the enzymatic activity (cf. Del Mar et al., 1979). The measurement is carried out at a temperature of 25° C., a pH of 8.6, and a wavelength of 410 nm. The measuring time is 5 min and the measuring interval is 20 s to 60 s. The protease activity is usually indicated in protease units (PE). Suitable protease activities amount for example to 2.25, 5 or 10 PE per ml of washing liquor, for example. However, the protease activity is not equal to zero.

An alternative test for establishing the proteolytic activity of the proteases is an optical measuring method, such as a photometric method. The appropriate test involves the protease-dependent cleavage of the substrate protein casein. This is cleaved by the protease into a multitude of smaller partial products. The totality of these partial products has an increased absorption at 290 nm compared with uncleaved casein, it being possible for this increased absorption to be determined using a photometer, and thus for a conclusion to be drawn regarding the enzymatic activity of the protease.

The protein concentration can be determined using known methods, for example the BCA method (bicinchoninic acid; 2,2'-bichinolyl-4,4'-dicarboxylic acid) or the Biuret method (A. G. Gornall, C. S. Bardawill and M. M. David, J. Biol. Chem., 177 (1948), pp. 751-766). The active protein concentration can be determined in this regard by titrating the active centers using a suitable irreversible inhibitor and determining the residual activity (cf. M. Bender et al., J. Am. Chem. Soc. 88, 24 (1966), pp. 5890-5913).

In addition to the amino acid alterations discussed above, proteases can have other amino acid alterations, in particular amino acid substitutions, insertions or deletions. Such proteases are, for example, further developed by targeted genetic modification, i.e. by mutagenesis methods, and optimized for specific applications or with regard to specific properties (for example with regard to their catalytic activity, stability, etc.). Furthermore, nucleic acids can be introduced into recombination approaches and can thus be used to generate completely novel proteases or other polypeptides.

The aim is to introduce targeted mutations such as substitutions, insertions or deletions into the known molecules in order, for example, to improve the cleaning performance of enzymes. For this purpose, in particular the surface charges and/or the isoelectric point of the molecules and thus their interactions with the substrate can be altered. For example, the net charge of the enzymes can be altered in order to influence the substrate binding, in particular for use in washing and cleaning agents. Alternatively or in addition, one or more corresponding mutations can increase the stability or catalytic activity of the protease and thus improve its cleaning performance. Advantageous properties of individual mutations, e.g. of individual substitutions, can complement one another. A protease which has already been optimized with regard to specific properties, for example with respect to its stability during storage, can therefore also be further developed.

For the description of substitutions relating to exactly one amino acid position (amino acid exchanges), the following convention is used herein: first, the naturally occurring amino acid is designated in the form of the internationally used one-letter code, followed by the associated sequence position and finally the inserted amino acid. Several exchanges within the same polypeptide chain are separated by slashes. In insertions, additional amino acids are named according to the sequence position. In the case of deletions, the missing amino acid is replaced by a symbol, for example a star or a dash, or a 4 is indicated before the corresponding position. For example, P9T describes the substitution of proline at position 9 by threonine, P9TH describes the insertion of histidine following the amino acid threonine at position 9 and P9* or ΔP9 describes the deletion of proline at position 9 and 130R/K describes the substitution at position 130 by lysine or arginine. This nomenclature is known to a person skilled in the art in the field of enzyme technology.

A protease is characterized in that it is obtainable from a protease as described above as the starting molecule by one-time or multiple conservative amino acid substitution, the protease in the numbering according to SEQ ID NO:1 having the above-described amino acid substitutions. The term "conservative amino acid substitution" means the exchange (substitution) of one amino acid residue for another amino acid residue, with this exchange not resulting in a change to the polarity or charge at the position of the exchanged amino acid, e.g. the exchange of a nonpolar amino acid residue for another nonpolar amino acid residue. Conservative amino acid substitutions include, for example: G=A=S, I=V=L=M, D=E, N=Q, K=R, Y=F, S=T, G=A=I=V=L=M=Y=F=W=P=S=T.

Alternatively or in addition, the protease is characterized in that it can be obtained from a protease as a starter molecule by means of fragmentation, deletion, insertion or substitution mutagenesis, and has an amino acid sequence which matches the starter molecule over a length of at least 200, 210, 220, 230, 240, 250, 260, 261, 262, 263, 264, 265, 266, 267, 268, 269, 270, 271, 272, 273 or 274 interconnected amino acids, the amino acid substitution(s) which are described herein and possibly contained in the starting molecule, still being present. I.e. when the proteases described herein are modified, the modification takes place such that the substitutions are maintained.

Alternatively or in addition, the protease is characterized in that it can be obtained from a protease as a starter molecule by means of fragmentation, deletion, insertion or substitution mutagenesis, and has an amino acid sequence which matches the starter molecule over a length of at least 200, 210, 220, 230, 240, 250, 260, 261, 262, 263, 264, 265, 266, 267, 268, 269, 270, 271, 272, 273 or 274 interconnected amino acids, the amino acid substitution(s) which are described herein and possibly contained in the starting molecule, still being present.

For example, it is possible to delete individual amino acids at the termini or in the loops of the enzyme without the proteolytic activity being lost or diminished in the process. Furthermore, such fragmentation or deletion, insertion or substitution mutagenesis can also for example reduce the allergenicity of the enzymes concerned and thus improve their overall applicability. Advantageously, the enzymes retain their proteolytic activity even after mutagenesis, i.e. their proteolytic activity corresponds at least to that of the starting enzyme, i.e. in a non-limiting embodiment the proteolytic activity is at least 80%, such as at least 90% of the activity of the starting enzyme. Further substitutions can also demonstrate advantageous effects. Both single and multiple interconnected amino acids can be exchanged for other amino acids.

Alternatively or additionally, the protease is characterized in that it is obtainable from a protease as a starting molecule by one-time or multiple conservative amino acid substitution, amino acid substitutions remaining unchanged.

The further amino acid positions are in this case defined by an alignment of the amino acid sequence of a protease with the amino acid sequence of the protease from *Bacillus pumilus*, as given in SEQ ID NO:1. Furthermore, the assignment of the positions depends on the mature protein. This assignment is also to be used in particular if the amino acid sequence of a protease comprises a higher number of amino acid residues than the protease from *Bacillus pumilus* according to SEQ ID NO:1. Proceeding from the abovementioned positions in the amino acid sequence of the protease from *Bacillus pumilus*, the alteration positions in a protease are those which are assigned to precisely these positions in an alignment.

Advantageous positions for sequence alterations, in particular substitutions, of the protease from *Bacillus pumilus* which are of particular significance when transferred to homologous positions of the proteases and which impart advantageous functional properties to the protease are therefore the positions which correspond in an alignment, i.e. in the numbering according to SEQ ID NO:1. At the positions mentioned, the following amino acid residues are present in the wild-type molecule of the protease from *Bacillus pumilus*: P9, A18, A29, A48, F61, A92, N99, D101, N130, G131, T133, N137, N144, V149, S156, T159, T162, G166, D172, A192, S199, S216, Y217, S224, N252, K265 and Q271.

Further confirmation of the correct assignment of the amino acids to be altered, i.e. in particular their functional correspondence, can be provided by comparative experiments, according to which the two positions assigned to one another on the basis of an alignment are altered in the same way in both compared proteases, and observations are made as to whether the enzymatic activity is altered in the same way in both cases. If, for example, an amino acid exchange in a specific position of the protease from *Bacillus pumilus* according to SEQ ID NO:1 is accompanied by an alteration of an enzymatic parameter, for example an increase in the KM value, and a corresponding alteration of the enzymatic parameter, for example likewise an increase in the KM value, is observed in a protease variant of which the amino acid exchange has been achieved by the same introduced amino acid, this can therefore be considered to be confirmation of the correct assignment.

All of these aspects are also applicable to the method for preparing a protease. Accordingly, a method further comprises one or more of the following method steps:

a) introducing a single or multiple conservative amino acid substitution into the protease, wherein the protease comprises
  (a) at the position corresponding to position 271, an amino acid substitution, in particular the amino acid substitution 271E; and
  (b1) at at least one of the positions corresponding to positions 18, 61, 92, 99, 137, 149, 156, 159, 162, 166, 172, 192, 199, 217 or 265, at least one further amino acid substitution; and/or
  (b2) at the position corresponding to position 9, an amino acid substitution, in particular selected from 9T, 9H, 9S and 9A, and at at least one position corresponding to positions 29, 48, 101, 130, 131, 133, 144, 217, 224 and 252, in particular 130, 133, 144, 217 and 252, a further amino acid substitution, for example A29G, A48V, D101E, N130D, N130S, N130H, G131D, G131N, G131S, G131K, T133K, T133R, T133Y, N144K, N144L, N144A, S224A, S224T or N252S;

b) modifying the amino acid sequence by means of fragmentation, deletion, insertion or substitution mutagenesis such that the protease comprises an amino acid sequence which matches the starter molecule over a length of at least 200, 210, 220, 230, 240, 250, 260, 261, 262, 263, 264, 265, 266, 267, 268, 269, 270, 271, 272, 273 or 274 interconnected amino acids, wherein the protease comprises
  (a) at the position corresponding to position 271, an amino acid substitution, in particular the amino acid substitution 271E; and
  (b1) at at least one of the positions corresponding to positions 18, 61, 92, 99, 137, 149, 156, 159, 162, 166, 172, 192, 199, 217 or 265, at least one further amino acid substitution; and/or
  (b2) at the position corresponding to position 9, an amino acid substitution, in particular selected from 9T, 9H, 9S and 9A, and at at least one position corresponding to positions 29, 48, 101, 130, 131, 133, 144, 217, 224 and 252, in particular 130, 133, 144, 217 and 252, a further amino acid substitution, for example A29G, A48V, D101E, N130D, N130S, N130H, G131D, G131N, G131S, G131K, T133K, T133R, T133Y, N144K, N144L, N144A, S224A, S224T or N252S.

All embodiments also apply to the method. In particular, each of the aforementioned proteases may additionally comprise an amino acid substitution at position 216 and/or 217 in the numbering according to SEQ ID NO:1, in particular 216C and/or 217M. However, in various embodiments the protease may have no substitution at position 216.

In further embodiments, the protease or the protease prepared by a method is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8% identical to one of the amino acid sequence specified in SEQ ID NO:1 over its entire length. Alternatively, the protease or the protease prepared by a method is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8% identical to one of the amino acid sequences given in SEQ ID Nos:3-12 and 16-25 over its entire length. The protease or the protease prepared by means of the method has an amino acid substitution at position 271, in particular 271E, and (i) in particular one or more of the amino acid substitutions 9T, 130D, 144K and 252T at position 9 and at least one of the positions corresponding to positions 29, 48, 101, 130, 131, 133, 144, 224 or 252, in each case based on the numbering according to SEQ ID NO:1, and/or (ii) at least one further amino acid substitution at at least one of the positions corresponding to positions 18, 61, 92, 99, 137, 149, 156, 159, 162, 166, 172, 192, 199, 217 or 265, in each case based on the numbering according to SEQ ID NO:1.

In embodiments, the one amino acid substitution is at least one amino acid substitution selected from the group consisting of P9T, P9H, P9T, P9A, A29G, A48V, D101E, N130D, N130S, N130H, G131D, G131N, G131S, G131K, T133K, T133R, T133Y, N144K, N144L, N144A, S224A, S224T, N252S and Q271E, in each case based on the numbering according to SEQ ID NO:1.

By way of example, the following amino acid substitutions may be mentioned: P9T, P9H, P9S or P9A, in particular P9T, and Q271E and optionally also S216C combined with one of (I) A48V, G131S, T133R and S224A; (II) G131D, T133R and S224A; (III) N130D, G131N, T133K and N144K; (IV) A29G, N130D, G131N and T133R; (V) N130D, G131S, T133K and S224A; (VI) N130D, G131N, T133K, N144L and N252S; (VII) G131S, N144K and S224T; (VIII) N130S, G131S, T133Y, N144L and S224A; (IX) D101E, G131N and S224A; or (X) N130H, G131S and S224A, the numbering being based in each case on the numbering according to SEQ ID NO:1.

In various embodiments, proteases are formed according to SEQ ID NO:1 having the following amino acid substitution variants: Q271E combined with one of (i) P9T, N130D, N144K and N252T; (ii) P9T, N130D, N144K, N252T and S156G; (iii) P9T, N130D, N144K, N252T and S156Y; (iv) P9T, N130D, N144K, N252T and Y217M; (v) P9T, N130D, N144K, N252T and N137K; (vi) N130D, N144K, N252T and F61Y; (vii) N130D, N144K, N252T and A92S; (viii) N130D, N144K, N252T, F61Y and A92S; (ix) N130D, N144K, N252T and T162S; (x) N130D, N144K, N252T and A192V; (xi) N130D, N144K, N252T, P9H, A18D and T159I; or (xii) P9T and D172G, the numbering being based in each case on the numbering according to SEQ ID NO:1. Further examples are the variants described above and in the examples.

The invention also relates to a protease described above which is additionally stabilized, in particular by one or more mutations, for example substitutions, or by coupling to a polymer. Increasing the stability in storage and/or during use, for example in the washing process, leads to the enzymatic activity lasting for longer and the cleaning performance thus being improved. In principle, all the stabilization options which are described in the prior art and/or are expedient are taken into consideration. Stabilizations may be achieved by mutation of the enzyme itself, as such stabilizations do not require any further working steps in addition to obtaining the enzyme. Examples of sequence alterations suitable for this purpose are mentioned above. Further suitable sequence changes are known from the prior art.

Further options for stabilization are, for example:

modifying the binding of metal ions, in particular the calcium binding sites, for example by exchanging one or more of the amino acid(s) involved in calcium binding with one or more negatively charged amino acids and/or by introducing sequence changes to at least one of the sequences of the two amino acids arginine/glycine;

protecting against the influence of denaturing agents such as surfactants by means of mutations which change the amino acid sequence on or at the surface of the protein;

exchanging amino acids which are near the N-terminus with amino acids that are presumed to be in contact with the rest of the molecule via non-covalent interactions and therefore contribute to maintaining the globular structure.

Non-limiting embodiments are those in which the enzyme is stabilized in a variety of ways, as a plurality of stabilizing mutations have an additive or synergistic effect.

The invention also relates to a protease as described above, which is characterized in that it has at least one chemical modification. A protease with such an alteration is referred to as a derivative, i.e. the protease is derivatized.

Within the context of various embodiments, derivatives are understood to mean proteins of which the pure amino acid chain has been chemically modified. Derivatizations of this kind can be carried out in vivo, for example, by the host cell that expresses the protein. In this regard, couplings of low-molecular-weight compounds such as of lipids or oligosaccharides are particularly noteworthy. However, derivatizations may also be carried out in vitro, for example by the chemical conversion of a side chain of an amino acid or by covalent bonding of another compound to the protein. For example, it is possible to couple amines to carboxyl groups of an enzyme in order to change the isoelectric point. Another compound of this kind may also be another protein which is bound to a protein via bifunctional chemical compounds, for example. Derivatization is likewise understood to mean covalent bonding to a macromolecular carrier, or non-covalent entrapment in suitable macromolecular cage structures. Derivatizations can, for example, influence the substrate specificity or the strength of the bond to the substrate or lead to temporary blocking of the enzymatic activity, if the coupled substance is an inhibitor. This may be expedient for the period of storage, for example. Such modifications can furthermore influence stability or enzymatic activity. They can also be used to reduce the allergenicity and/or immunogenicity of the protein and thereby increase the skin compatibility thereof. For example, couplings with macromolecular compounds, such as polyethylene glycol, can improve the protein with regard to stability and/or skin compatibility.

Derivatives of a protein can be understood, in the broadest sense, to also mean preparations of said proteins. Depending on its extraction, processing or preparation, a protein can be combined with various other substances, for example from the culture of the producing microorganisms. A protein can also be combined in a targeted manner with other substances, for example in order to increase its storage stability. This is also irrespective of whether or not said protein actually develops this enzymatic activity in a specific preparation, as it may be desirable that it has no or only minimal activity in storage, and develops its enzymatic function only at the point of use. This can be controlled by corresponding accompanying substances, for example. In particular, the joint preparation of proteases with specific inhibitors is possible in this regard.

Of all the proteases or protease variants and/or derivatives described above, those of which the catalytic activity corresponds to at least one of those of the proteases according to SEQ ID Nos: 3-12 and 16-25, and/or of which the cleaning performance corresponds to at least one of those of the proteases according to SEQ ID Nos: 3-12 or 16-25, are suitable, the cleaning performance being determined in a washing system as described above.

In a further aspect, a protease may have an amino acid sequence which has at least 70% sequence identity with the amino acid sequence given in SEQ ID NO:1 over its entire length and which comprises at least one amino acid substitution selected from the group consisting of G131N, T133K, T133Y, N144L or N252S, in each case based on the numbering according to SEQ ID NO:1. In such an embodiment, the protease has either no substitutions at positions 9 and 271, and optionally also no substitution at position 216, or it has a substitution at one of positions 9 and 271, and optionally also a substitution at position 216.

This also applies in particular to the optionally present further substitutions and the sequence identity with SEQ ID NO:1, which may be 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8%.

The invention also relates to a nucleic acid which codes for a protease, as well as to a vector containing such a nucleic acid, in particular a cloning vector or an expression vector.

These may be DNA or RNA molecules. They can be present as a single strand, as a single strand that is complementary to this single strand, or as a double strand. In particular in the case of DNA molecules, the sequences of the two complementary strands must be taken into account in all three possible reading frames. Furthermore, it should be noted that different codons, i.e. base triplets, can code for the same amino acids such that a particular amino acid sequence can be coded by a plurality of different nucleic acids. Due to this degeneracy of the genetic code, all of the nucleic acid sequences which can code any of the proteases described above are included in this subject matter. A person skilled in the art is able to determine these nucleic acid sequences unequivocally since, despite the degeneracy of the genetic code, defined amino acids can be assigned to individual codons. Therefore, a person skilled in the art proceeding from an amino acid sequence can easily determine nucleic acids coding for said amino acid sequence. Furthermore, in the case of nucleic acids, one or more codons may be replaced by synonymous codons. This aspect relates in particular to the heterologous expression of the enzymes. Thus, every organism, for example a host cell of a production strain, has a particular codon usage. Codon usage is understood to mean the translation of the genetic code into amino acids by the particular organism. Bottlenecks can occur in the protein biosynthesis if the codons on the nucleic acid in the organism are faced with a comparatively small number of loaded tRNA molecules. Although coding for the same amino acid, this results in a codon being translated less efficiently in the organism than a synonymous codon coding for the same amino acid. Due to the presence of a higher number of tRNA molecules for the synonymous codon, it can be translated more efficiently in the organism.

Using methods which are currently generally known, such as chemical synthesis or the polymerase chain reaction (PCR), in conjunction with molecular-biological and/or protein-chemical standard methods, it is possible for a person skilled in the art to produce the corresponding nucleic acids and even complete genes on the basis of known DNA and/or amino acid sequences. Such methods are known, for example, from Sambrook, J., Fritsch, E. F. and Maniatis, T. 2001. Molecular cloning: a laboratory manual, 3rd edition, Cold Spring Laboratory Press.

In the context of various embodiments, vectors are understood to mean elements which consist of nucleic acids and which contain a nucleic acid as a characterizing nucleic acid range. They are able to establish these as a stable genetic element in a species or cell line over several generations or cell divisions. Vectors are specific plasmids, i.e. circular genetic elements, in particular for use in bacteria. In the context of various embodiments, a nucleic acid is cloned into a vector. The vectors include, for example, those originating from bacterial plasmids, viruses or bacteriophages, or predominantly synthetic vectors or plasmids with elements of a wide variety of origins. Using the further genetic elements which are present in each case, vectors can be established as stable units in the host cells in question over several generations. They may be present as separate units in an extrachromosomal manner or integrated into a chromosome or chromosomal DNA.

Expression vectors comprise nucleic acid sequences which enable them to replicate in the host cells containing them, such as microorganisms, e.g. bacteria, and to express a contained nucleic acid there. The expression is in particular influenced by the promoter(s) that regulate the transcription. In principle, the expression can take place by the natural promoter originally located before the nucleic acid to be expressed, but also by a promoter of the host cell provided on the expression vector or also by a modified or completely different promoter of another organism or another host cell. In the present case, at least one promoter is provided for the expression of a nucleic acid and used for the expression thereof. Furthermore, expression vectors can be regulatable, for example by changing the cultivation conditions or when a specific cell density of the host cells containing them is reached or by addition of specific substances, in particular activators of gene expression. An example of such a substance is the galactose derivative isopropyl-p-D-thiogalactopyranoside (IPTG), which is used as an activator of the bacterial lactose operon (lac operon). In contrast with expression vectors, the nucleic acid contained is not expressed in cloning vectors.

The invention also relates to a non-human host cell which contains a nucleic acid or a vector or which contains a protease, in particular one which secretes the protease into the medium surrounding the host cell. A nucleic acid or a vector is transformed into a microorganism, which then represents a host cell. Alternatively, individual components, i.e. nucleic acid parts or fragments of a nucleic acid can be introduced into a host cell such that the resulting host cell contains a nucleic acid or a vector. This procedure is particularly suitable when the host cell already contains one or more constituents of a nucleic acid or a vector and the further constituents are then supplemented accordingly. Methods for transforming cells are established in the prior art and are well known to a person skilled in the art. In principle, all cells, i.e. prokaryotic or eukaryotic cells, are suitable as host cells. Host cells that can be managed in a genetically advantageous manner, for example in terms of the transformation with the nucleic acid or the vector and the stable establishment thereof, are suitable, for example unicellular fungi or bacteria. Furthermore, host cells are characterized by good microbiological and biotechnological handleability. This relates, for example, to ease of culturing, high growth rates, low demands on fermentation media, and good production and secretion rates for foreign proteins. Non-limiting host cells secrete the (transgenically) expressed protein into the medium surrounding the host cells. Furthermore, the proteases can be modified by the cells producing them after their production, for example by attachment of sugar molecules, formylations, aminations, etc. Such post-translational modifications can functionally influence the protease.

Other non-limiting embodiments are those host cells of which the activity can be regulated on account of genetic regulatory elements, which are, for example, made available on the vector but may also be present in these cells from the outset. These host cells may be induced to express, for example by the controlled addition of chemical compounds which are used as activators, by changing the culturing conditions, or upon reaching a certain cell density. This enables an economical production of the proteins. An example of such a compound is IPTG as described above.

Prokaryotic or bacterial cells may be host cells. Bacteria are characterized by short generation times and low demands on cultivation conditions. As a result, cost-effective cultivation methods or production methods can be established. In addition, a person skilled in the art has a wealth of experience in the case of bacteria in fermentation technology. For a specific production, gram-negative or gram-positive bacteria may be suitable for a wide variety of reasons to be determined experimentally in individual cases, such as nutrient sources, product formation rate, time requirement, etc.

In the case of gram-negative bacteria, such as *Escherichia coli*, a large number of proteins are secreted into the periplasmic space, i.e. into the compartment between the two membranes enclosing the cells. This may be advantageous for particular applications. Furthermore, gram-negative bacteria can also be designed such that they eject the expressed proteins not only into the periplasmic space, but into the medium surrounding the bacterium. In contrast, gram-positive bacteria such as bacilli or actinomycetes or other representatives of Actinomycetales have no outer membrane, and therefore secreted proteins are released immediately into the medium surrounding the bacteria, usually the nutrient medium, from which the expressed proteins can be purified. They can be isolated directly from the medium or further processed. In addition, gram-positive bacteria are related or identical to most of the origin organisms for technically significant enzymes and usually even form comparable enzymes, meaning that they have a similar codon usage and the protein synthesizer is naturally aligned accordingly.

Host cells may be altered in terms of their requirements for the culture conditions, may have different or additional selection markers or may express other or additional proteins. In particular, this may also involve those host cells which transgenically express several proteins or enzymes.

The present invention is applicable in principle to all microorganisms, in particular to all fermentable microorganisms, such as those of the genus *Bacillus*, and leads to it being possible to produce proteins by the use of such microorganisms. Such microorganisms then represent host cells.

In a further embodiment, the host cell is characterized in that it is a bacterium, such as one selected from the group of the genera of *Escherichia*, *Klebsiella*, *Bacillus*, *Staphylococcus*, *Corynebacterium*, *Arthrobacter*, *Streptomyces*, *Stenotrophomonas* and *Pseudomonas*, such as one selected from the group of *Escherichia coli*, *Klebsiella planticola*, *Bacillus licheniformis*, *Bacillus lentus*, *Bacillus amyloliquefaciens*, *Bacillus subtilis*, *Bacillus alcalophilus*, *Bacillus globigii*, *Bacillus gibsonii*, *Bacillus clausii*, *Bacillus halodurans*, *Bacillus pumilus*, *Staphylococcus carnosus*, *Corynebacterium glutamicum*, *Arthrobacter oxidans*, *Streptomyces lividans*, *Streptomyces coelicolor* and *Stenotrophomonas maltophilia*.

The host cell may also be a eukaryotic cell, however, which is characterized in that it has a cell nucleus. The invention therefore also relates to a host cell which is characterized in that it has a cell nucleus. In contrast with prokaryotic cells, eukaryotic cells are capable of post-translationally modifying the protein formed. Examples thereof are fungi such as *Actinomycetes* or yeasts such as *Saccharomyces* or *Kluyveromyces*. This may be particularly advantageous, for example, when, in the context of their synthesis, the proteins undergo specific modifications which allow such systems. Modifications carried out by eukaryotic systems, in particular in connection with the protein synthesis, include, for example, the binding of low-molecular-weight compounds such as membrane anchors or oligosaccharides. Such oligosaccharide modifications may be desirable, for example, to lower the allergenicity of an expressed protein. Co-expression with the enzymes naturally formed by such cells, such as cellulases, may be advantageous. Furthermore, for example, thermophilic fungal expression systems may be particularly suitable for the expression of temperature-resistant proteins or variants.

The host cells are cultivated and fermented in the conventional way, for example in discontinuous or continuous systems. In the first case, a suitable culture medium is inoculated with the host cells, and the product is harvested from the medium after a period of time that is to be experimentally determined. Continuous fermentations are characterized by the achievement of a flow equilibrium, in which cells partially die over a comparatively long period of time but also grow back and the protein formed can be removed from the medium at the same time.

Host cells are used to prepare proteases. The invention therefore also relates to a method for preparing a protease, comprising
 a) cultivating a host cell, and
 b) isolating the protease from the culture medium or from the host cell.

This subject matter comprises fermentation processes. Fermentation processes are known per se from the prior art and represent the actual large-scale production step, usually followed by a suitable purification method of the produced product, for example the proteases. All fermentation processes which are based on a corresponding method for preparing a protease constitute embodiments of this subject matter.

Fermentation methods which are characterized in that the fermentation is carried out via an inflow strategy are considered in particular. In this case, the media components that are consumed by the continuous culturing are fed. As a result, considerable increases can be achieved both in the cell density and in the cell mass or dry mass and/or in particular in the activity of the protease of interest. Furthermore, the fermentation may also be designed in such a way that undesirable metabolic products are filtered out, or neutralized by adding a buffer or counterions which are appropriate in each case.

The protease prepared can be harvested from the fermentation medium. Such a fermentation process may be more suitable as compared to isolation of the protease from the host cell, i.e. product preparation from the cell mass (dry matter), but requires the provision of suitable host cells or one or more suitable secretion markers or mechanisms and/or transport systems for the host cells to secrete the protease into the fermentation medium. Without secretion, the protease can alternatively be isolated from the host cell, i.e. purified from the cell mass, for example by precipitation with ammonium sulphate or ethanol, or by chromatographic purification.

All of the above-mentioned aspects can be combined into methods in order to prepare protease.

The invention also relates to an agent which is characterized in that it contains a protease as described above. The agent is a washing or cleaning agent.

This subject matter includes all conceivable types of washing or cleaning agent, both concentrates and undiluted agents, for use on a commercial scale, in washing machines or in hand washing or cleaning. These include washing agents for textiles, carpets, or natural fibers, for which the term washing agent is used. These also include, for example, dishwashing detergents for dishwashers or manual dishwashing detergents or cleaners for hard surfaces such as metal, glass, porcelain, ceramics, tiles, stone, painted surfaces, plastics materials, wood or leather, for which the term cleaning agent is used, i.e. in addition to manual and machine dishwashing detergents, for example also scouring agents, glass cleaners, toilet scenters, etc. The washing and cleaning agents may also include auxiliary washing agents, which are added to the actual washing agent when washing textiles manually or using a machine in order to achieve an additional effect. Furthermore, washing and cleaning agents in the scope also include textile pre-treatment and post-treatment agents, i.e. those agents with which the item of laundry is brought into contact before the actual washing cycle, for example to loosen stubborn soiling, and also those agents which give the laundry further desirable properties such as a pleasant feel, crease resistance or low static charge in a step subsequent to the actual textile wash. Inter alia, softeners are included in the last-mentioned agents.

The washing or cleaning agents, which may be in the form of powdered solids, in further-compacted particulate form, homogeneous solutions or suspensions, may contain, in addition to a protease, all known ingredients conventional in such agents, with at least one other ingredient being present in the agent. The agents may in particular contain surfactants, builders, peroxygen compounds or bleach activators. They may also contain water-miscible organic solvents, further enzymes, sequestering agents, electrolytes, pH regulators and/or further auxiliaries such as optical brighteners, graying inhibitors, foam regulators, as well as dyes and fragrances, and combinations thereof.

In particular, a combination of a protease with one or more further ingredients of the agent is advantageous, since, in non-limiting embodiments, such an agent has improved cleaning performance by virtue of resulting synergisms. In particular, combining a protease with a surfactant and/or a builder and/or a peroxygen compound and/or a bleach activator can result in such a synergism. However, in embodiments, the agent may not contain boric acid.

Advantageous ingredients of agents are disclosed in international patent application WO2009/121725, starting at the penultimate paragraph of page 5 and ending after the second paragraph on page 13. Reference is expressly made to this disclosure and the disclosure therein is incorporated in the present patent application by reference.

An agent advantageously contains the protease in an amount of from 2 µg to 20 mg, such as from 5 µg to 17.5 mg, alternatively from 20 µg to 15 mg or from 50 µg to 10 mg per g of the agent. In various embodiments, the concentration of the protease (active enzyme) described herein in the agent is >0 to 1 wt. %, such as 0.001 to 0.1 wt. %, based on the total weight of the agent or composition. Further, the protease contained in the agent, and/or other ingredients of the agent, may be coated with a substance which is impermeable to the enzyme at room temperature or in the absence of water, and which becomes permeable to the enzyme under conditions of use of the agent. Such an embodiment is thus characterized in that the protease is coated with a substance which is impermeable to the protease at room temperature or in the absence of water. Furthermore, the washing or cleaning agent itself can be packed in a container, such as an air-permeable container, from which it is released shortly before use or during the washing process.

In further embodiments, the agent is characterized in that it
(a) is present in solid form, in particular as a flowable powder having a bulk density of from 300 g/l to 1200 g/l, in particular from 500 g/l to 900 g/l, or
(b) is present in pasty or liquid form, and/or
(c) is present in the form of a gel or in the form of dosing pouches, and/or
(d) is present as a single-component system, or
(e) is divided into a plurality of components.

These embodiments include all solid, powdered, liquid, gel or paste administration forms of agents, which may optionally also consist of a plurality of phases and can be present in compressed or uncompressed form. The agent may be present as a free-flowing powder, having a bulk density of from 300 g/l to 1200 g/l, in particular from 500 g/l to 900 g/l or 600 g/l to 850 g/l. The solid administration forms of the agent also include extrudates, granules, tablets or pouches. Alternatively, the agent may also be in liquid, gel or paste form, for example in the form of a non-aqueous liquid washing agent or a non-aqueous paste or in the form of an aqueous liquid washing agent or a water-containing paste. Moreover, the agent may be present as a single-component system. Such agents consist of one phase. Alternatively, an agent may consist of a plurality of phases. Such an agent is therefore divided into a plurality of components.

Washing or cleaning agents may contain only one protease. Alternatively, they may also contain other hydrolytic enzymes or other enzymes in a concentration that is expedient for the effectiveness of the agent. A further embodiment is therefore represented by agents which further comprise one or more further enzymes. All enzymes which can develop catalytic activity in a washing or cleaning agent, in particular a lipase, amylase, cellulase, hemicellulase, mannanase, tannanase, xylanase, xanthanase, xyloglucanase, ß-glucosidase, pectinase, carrageenanase, perhydrolase, oxidase, oxidoreductase or another protease which is distinct from the protease, and mixtures thereof, can be used as further enzymes. Further enzymes are advantageously contained in the agent in an amount of from $1\times10^{-8}$ to 5 wt. %, based on active protein. Each further enzyme is contained in agents in an amount of from $1\times10^{-7}$ to 3 wt. %, from 0.00001 to 1 wt. %, from 0.00005 to 0.5 wt. %, from 0.0001 to 0.1 wt. % or from 0.0001 to 0.05 wt. %, based on active protein. The enzymes exhibit synergistic cleaning performance against specific soiling or stains, i.e. the enzymes contained in the agent composition support one another in their cleaning performance. There is synergism between the protease and a further enzyme of an agent, including in particular between said protease and an amylase and/or a lipase and/or a mannanase and/or a cellulase and/or a pectinase. Synergistic effects can arise not only between different enzymes, but also between one or more enzymes and other ingredients of the agent.

In the cleaning agents described herein, the enzymes to be used may furthermore be produced together with accompanying substances, for example from fermentation. In liquid formulations, the enzymes are used as enzyme liquid formulations.

The enzymes are generally not provided in the form of pure protein, but rather in the form of stabilized, storable and transportable preparations. These ready-made preparations include, for example, the solid preparations obtained through granulation, extrusion, or lyophilization or, particularly in the case of liquid or gel agents, solutions of the enzymes, advantageously maximally concentrated, low-water, and/or supplemented with stabilizers or other auxiliaries.

Alternatively, the enzymes can also be encapsulated for both the solid and the liquid dosage form, for example by spray-drying or extrusion of the enzyme solution together with a natural polymer or in the form of capsules, for example those in which the enzymes are entrapped in a set gel, or in those of the core-shell type in which an enzyme-containing core is coated with a water-, air-, and/or chemical-impermeable protective layer. In the case of overlaid layers, other active ingredients, such as stabilizers, emulsifiers, pigments, bleaching agents, or dyes, can be additionally applied. Such capsules are applied using inherently known methods, for example by shaking or roll granulation or in fluidized bed processes. Such granules are advantageously low in dust, for example due to the application of polymeric film-formers, and stable in storage due to the coating.

Moreover, it is possible to formulate two or more enzymes together, so that a single granule exhibits a plurality of enzyme activities.

The enzymes can also be incorporated in water-soluble films, such as those used in the formulation of washing and cleaning agents in a unit dosage form. Such a film allows the release of the enzymes following contact with water. As used herein, "water-soluble" refers to a film structure that is completely water-soluble. In a non-limiting embodiment, such a film consists of (fully or partially hydrolyzed) polyvinyl alcohol (PVA).

The invention also relates to a method for cleaning textiles or hard surfaces, which is characterized in that an agent is used in at least one method step, or in that a protease becomes catalytically active in at least one method step, in particular such that the protease is used in an amount of from 40 µg to 4 g, such as from 50 µg to 3 g, alternatively from 100 µg to 2 g, or from 200 µg to 1 g.

In various embodiments, the method described above is characterized in that the protease is used at a temperature of from 0 to 100° C., such as 0 to 60° C., alternatively 20 to 40° C. or at 20 or 25° C.

These include both manual and mechanical methods, with mechanical methods being suitable. Methods for cleaning textiles are generally characterized in that various substances that have a cleaning effect are applied to the item to be cleaned in a plurality of method steps and washed off after the contact time, or in that the item to be cleaned is otherwise treated with a washing agent or a solution or dilution of this agent. The same applies to methods for cleaning all materials other than textiles, in particular hard surfaces. All conceivable washing or cleaning methods can be enhanced in at least one of the method steps by the use of a washing or cleaning agent or a protease, and then represent embodiments. All aspects, objects, and embodiments described for the protease and agents containing it are also applicable to this subject matter. Therefore, reference is expressly made at this point to the disclosure at the appropriate point with the note that this disclosure also applies to the above-mentioned methods.

Since proteases naturally already have hydrolytic activity and also exhibit this in media which otherwise have no cleaning power, for example in a simple buffer, a single and/or the sole step of such a method can consist in the protease, which is the only cleaning-active component, being brought into contact with the stain, such as in a buffer solution or in water. This represents a further embodiment of this subject matter.

Alternative embodiments of this subject matter are also represented by methods for treating textile raw materials or for textile care, in which a protease becomes active in at least one method step. Among these, methods for textile raw materials, fibers or textiles with natural components are suitable, such as those with wool or silk.

Finally, the invention also encompasses the use of the proteases described herein in washing or cleaning agents, for example as described above, for the (improved) removal of protein-containing stains, for example from textiles or hard surfaces. In various embodiments of this use, the protease in the washing or cleaning agent is stored for 3 or more days, 4 or more days, 7 or more days, 10 or more days, 12 or more days, 14 or more days, 21 or more days or 28 or more days before a washing or cleaning process.

All aspects, objects, and embodiments described for the protease and agents containing it are also applicable to this subject matter of the invention. Therefore, reference is expressly made at this point to the disclosure at the appropriate point with the note that this disclosure also applies to the above-mentioned use.

EXAMPLES

Overview of the Mutations:

This invention relates to a subtilisin-type alkaline protease from *Bacillus pumilus*. From this protease (wild-type *Bacillus pumilus* DSM 18097 protease according to SEQ ID NO:1), variants were produced by random mutagenesis, which were then screened, inter alia for improved washing performance and/or enzyme stability. In this way, two performance-enhanced mutants (mutant 1 [SEQ ID NO:13] and mutant 2 [SEQ ID NO:2]) were generated from the wild-type protease (SEQ ID NO:1) mentioned above in a first round by error-prone mutagenesis. Both of these mutants were subject to an independent, second error-prone round. In this second round of mutation, mutants 3-12 according to SEQ ID Nos. 3-12 were generated. Therefore, all of mutants 3-12 mentioned here also carry at least some of the mutations of mutants 1 or 2. In a third round, other performance-enhanced mutants (mutant 1 [SEQ ID NO:14], mutant 2 [SEQ ID NO:15], mutant 3 [SEQ ID NO:16]) were generated by error-prone mutagenesis. These mutants were subject to another error-prone round (fourth round), and several saturation mutagenesis processes were carried out at specific positions. Moreover, several mutants have been produced by targeted generation of synthetic genes. In this fourth round of mutation, mutants 16-24 according to SEQ ID Nos. 17-25 were generated, as well as mutants 25-52.

| Variant | | Amino acid substitutions relative to SEQ ID NO: 1 | | | | | | SEQ ID NO. |
|---|---|---|---|---|---|---|---|---|
| Mutant 1 | P9T | Q271E | S216C | | | | | 13 |
| Mutant 2 | P9T | Q271E | S216C | T133R | S224A | | | 2 |
| Mutant 3 | P9T | Q271E | S216C | A48V | G131S | T133R | S224A | 3 |
| Mutant 4 | P9T | Q271E | S216C | G131D | T133R | S224A | | 4 |
| Mutant 5 | P9T | Q271E | S216C | N130D | G131N | T133K | N144K | 5 |
| Mutant 6 | P9T | Q271E | S216C | A29G | N130D | G131N | T133R | 6 |
| Mutant 7 | P9T | Q271E | S216C | N130D | G131S | T131K | S224A | 7 |
| Mutant 8 | P9T | Q271E | S216C | N130D | G131N | T133K | N144L N252S | 8 |
| Mutant 9 | P9T | Q271E | S216C | G131S | N144K | S224T | | 9 |
| Mutant | P9T | Q271E | S216C | N130S | G131S | T133Y | N144L S224A | 10 |
| Mutant | P9T | Q271E | S216C | D101E | G131N | S224A | | 11 |
| Mutant | P9T | Q271E | S216C | N130H | G131S | S224A | | 12 |
| Mutant | P9T | | | | Q271E | | | 14 |
| Mutant | | N130D | N144K | N252T | Q271E | | | 15 |
| Mutant | P9T | N130D | N144K | N252T | Q271E | | | 16 |
| Mutant | P9T | N130D | N144K | N252T | Q271E | S156G | | 17 |
| Mutant | P9T | N130D | N144K | N252T | Q271E | S156Y | | 18 |
| Mutant | P9T | N130D | N144K | N252T | Q271E | Y217M | | 19 |
| Mutant | P9T | N130D | N144K | N252T | Q271E | N137K | | 20 |
| Mutant | | N130D | N144K | N252T | Q271E | F61Y | A92S | 21 |
| Mutant | | N130D | N144K | N252T | Q271E | T162S | | 22 |
| Mutant | | N130D | N144K | N252T | Q271E | A192V | | 23 |
| Mutant | P9H | N130D | N144K | N252T | Q271E | A18D | T159I | 24 |
| Mutant | P9T | | | | Q271E | D172G | | 25 |
| Mutant | P9T | N130D | N144K | N252T | Q271E | T133R | | |
| Mutant | P9T | N130D | N144K | N252T | Q271E | T133K | | |
| Mutant | P9T | N130D | N144K | N252T | Q271E | S224A | | |
| Mutant | P9T | N130D | N144K | N252T | Q271E | S224A | T133R | |
| Mutant | P9T | N130D | N144K | N252T | Q271E | D172G | | |
| Mutant | P9T | N130D | N144K | N252T | Q271E | D172P | | |
| Mutant | P9T | N130D | N144K | N252T | Q271E | V149I | | |
| Mutant | P9T | N130D | N144K | N252T | Q271E | N99Y | | |
| Mutant | P9T | N130D | N144K | N252T | Q271E | Q62S | | |
| Mutant | P9T | N130D | N144K | N252T | Q271E | N137K | | |
| Mutant | P9T | N130D | N144K | N252T | Q271E | T162S | | |
| Mutant | P9T | N130D | N144K | N252T | Q271E | Y217M | T133R | |
| Mutant | P9T | N130D | N144K | N252T | Q271E | Y217M | | |
| Mutant | P9T | N130D | N144K | N252T | Q271E | Y217M | T133A | |
| Mutant | P9T | N130D | N144K | N252T | Q271E | Y217M | A192V | |
| Mutant | P9T | N130D | N144K | N252T | Q271E | T133A | A192V | |
| Mutant | P9T | N130D | N144K | N252T | Q271E | T162S | A192V | |
| Mutant | P9T | N130D | N144K | N252T | Q271E | T162S | Y217M | |
| Mutant | P9T | N130D | N144K | N252T | Q271E | T162S | T133A | |
| Mutant | P9T | N130D | N144K | N252T | Q271E | T162S | Y217M A192V | |
| Mutant | P9T | N130D | N144K | N252T | Q271E | T162S | Y217M A192V T133A | |
| Mutant | P9T | N130D | N144K | N252T | Q271E | T162S | Y217M T133A | |
| Mutant | P9T | N130D | N144K | N252T | Q271E | T162S | A192V T133A | |
| Mutant | P9T | N130D | N144K | N252T | Q271E | T133A | K265A | |
| Mutant | P9T | N130D | N144K | N252T | Q271E | T133A | S199M | |
| Mutant | P9T | N130D | N144K | N252T | Q271E | T133A | G166M | |
| Mutant | P9T | N130D | N144K | N252T | Q271E | T162S | G166M | |
| Mutant | P9T | N130D | N144K | N252T | Q271E | A192V | | |

Washing Agent Matrix Used

The following washing agent matrices (commercially available, without enzymes, opt. brighteners, perfume and dyes) were used for the washing tests:

Washing Test 2:

| Chemical name | Wt. % active substance in the | Wt. % active substance in the formulation |
|---|---|---|
| Demineralized water | 100 | Remainder |
| Alkylbenzene sulfonic acid | 96 | 12-18 |
| Anionic surfactants | 70 | 4-8 |
| $C_{12}$-$C_{18}$ fatty acid Na salt | 30 | 2-4 |
| Non-ionic surfactants | 100 | 8-14 |
| Phosphonate | 60 | 0.5-2 |
| Citric acid | 100 | 3-5 |
| NaOH | 50 | 0.5-2 |
| Defoamer | 100 | <1% |
| Glycerol | 99.5 | 1-3 |
| 1,2-propanediol | 100 | 8-12 |
| Monoethanolamine | 100 | 4-8 |
| Soil repellent polymer | 30 | 0.5-1 |
| Protease stabilizer | 100 | 0.5-1.5 |

Without opt. brighteners, perfume, dye and enzymes.
Dosage 3.17 g/L

Washing Test 1:

| Chemical name | Wt. % active substance in the | Wt. % active substance in the formulation |
|---|---|---|
| Demineralized water | 100 | Remainder |
| Alkylbenzene sulfonic acid | 96 | 4.4 |
| Anionic surfactants | 70 | 5.6 |
| $C_{12}$-$C_{18}$ fatty acid Na salt | 30 | 2.4 |
| Non-ionic surfactants | 100 | 4.4 |
| Phosphonates | 40 | 0.2 |
| Citric acid | 100 | 1.4 |
| NaOH | 50 | 0.95 |
| Defoamer | t.q. | 0.01 |
| Glycerol | 100 | 2 |
| Preservative | 100 | 0.08 |
| Ethanol | 93 | 1 |

Without opt. brighteners, perfume, dye and enzymes.
Dosage 4.7 g/L

Protease Activity Assays

The activity of the protease is determined by the release of the chromophore para-nitroaniline from the substrate succinyl alanine-alanine-proline-phenylalanine-para-nitroanilide (AAPFpNA; Bachem L-1400). The release of the pNA causes an increase in absorbance at 410 nm, the temporal progression of which is a measure of the enzymatic activity.

The measurement was carried out at a temperature of 25° C., a pH of 8.6, and a wavelength of 410 nm. The measuring time was 5 min at a measuring interval of 20 to 60 seconds.

Measurement Approach:
10 µL AAPF solution (70 mg/mL)
1000 µL Tris-HCl (0.1 M; pH 8.6 with 0.1% Brij 35)
10 µL diluted protease solution
Kinetics created over 5 min at 25° C. (410 nm)
Mini Washing Test and Results
Washing Test 1:

Washing test with *Bacillus subtilis* culture supernatants containing the screened protease mutants by heterologous expression. The supernatants were used in washing agents in the equivalent activity to the benchmark=starting molecule for this mutagenesis round (mutants 1 and 2 according to SEQ ID Nos. 1 and 2) at a market-standard concentration for proteases.

Conditions: 40° C., 16° dH water, 1 h
Stains:
1. CFT CS038
2. CFT PC-10
3. WFK 10N
4. CFT C-03
5. EMPA 112
6. CFT C-05

Punched-out pieces of fabric (diameter=10 mm) provided in a microtiter plate, the washing liquor to pre-heated to 40° C., final concentration 4.7 g/L, the liquor and enzyme added to the stain, incubated for 1 h at 40° C. and 600 rpm, then the stain rinsed several times with clear water, left to dry and the brightness determined using a color-measuring device. The brighter the fabric becomes, the better the cleaning performance. The L value=brightness was measured here, the higher the brighter. The sum of the 6 stains is given in % based on the mutant according to SEQ ID NO:13 or the mutant according to SEQ ID NO:2.

| Variant | Catalytic activity (based on cationic activity of mutant 2 (SEQ ID NO: 2)) | |
|---|---|---|
| | 40° C. | 20° C. |
| Mutant 2 | 100% | 100% |
| Mutant 3 | 112% | 117% |
| Mutant 4 | 112% | 110% |

Both variants exhibit increased washing performance in comparison with the starting variant (mutant 2 according to SEQ ID NO:2). The improvements are clear at 40° C. and 20° C.

| Variant | Catalytic activity (based on cationic activity of mutant 1 (SEQ ID NO: 13)) | |
|---|---|---|
| | 40° C. | 20° C. |
| Mutant 1 | 100% | 100% |
| Mutant 5 | 129% | 138% |
| Mutant 6 | 113% | 148% |
| Mutant 7 | 129% | 124% |
| Mutant 8 | 126% | 121% |
| Mutant 9 | 134% | 117% |
| Mutant 10 | 118% | 124% |
| Mutant 11 | 118% | 117% |
| Mutant 12 | 121% | 131% |

All variants exhibit increased washing performance in comparison with the starting variant (mutant 1 according to SEQ ID NO:13). The improvements are clear at 40° C. and 20° C.

Washing Test 2:

Washing test with *Bacillus subtilis* culture supernatants containing the screened protease mutants by heterologous expression. The supernatants are used in washing agents in the equivalent activity to the benchmark=wild type (according to SEQ ID NO:1) at a market-standard concentration for proteases. The mutants are all based on the washing performance of the wild type, which is set equal to 100% (sum of the 7 stains, corrected by the performance of the washing agent alone).

Conditions: 40° C., 16° dH water, 1 h
Stains:
1. CFT CS038
2. CFT PC-10
3. WFK 10N

4. CFT C-03
5. EMPA 112
6. CFT C-05
7. H-MR-B

Punched-out pieces of fabric (diameter=10 mm) provided in microtiter plates, the washing liquor to pre-heated to 40° C., final concentration 3.17 g/L, the liquor and enzyme added to the stain, incubated for 1 h at 40° C. and 600 rpm, then the stain rinsed several times with clear water, left to dry and the brightness determined using a color-measuring device. The brighter the fabric becomes, the better the cleaning performance. The L value=brightness was measured here, the higher the brighter. The sum of the 7 stains is given in % based on the wild type according to SEQ ID NO:1 corrected by the performance of the washing agent without protease.

| Variant | Performance in washing test at 40° C. (based on performance of wild type (SEQ ID NO: 1)) |
|---|---|
| Wild type | 100% |
| Mutant 13 | 103% |
| Mutant 15 | 105% |
| Mutant 16 | 109% |
| Mutant 17 | 110% |
| Mutant 18 | 106.5% |
| Mutant 19 | 106% |
| Mutant 20 | 113% |
| Mutant 21 | 109% |
| Mutant 22 | 107.5% |
| Mutant 23 | 101.5% |
| Mutant 24 | 101.5% |

All variants exhibit increased washing performance in comparison with the wild type according to SEQ ID NO:1.

The same washing test was performed again at 20° C., using mutant 3 as a reference.

| Variant | Performance in washing test at 20° C. (based on performance of mutant 3 (SEQ ID NO: 4)) |
|---|---|
| Mutant 15 | 100% |
| Mutant 25 | 105% |
| Mutant 26 | 107% |
| Mutant 27 | 107% |
| Mutant 28 | 113% |

A further washing test was, as described above, carried out at 40° C. with the stain CFT PC-10, using mutant 15 as a reference.

| Variant | Performance in washing test at 40° C. (based on performance of mutant 3 (SEQ ID NO: 4)) |
|---|---|
| Mutant 15 | 100% |
| Mutant 29 | 117% |
| Mutant 30 | 118% |
| Mutant 31 | 108% |
| Mutant 32 | 108% |
| Mutant 33 | 117% |
| Mutant 34 | 121% |
| Mutant 35 | 116% |
| Mutant 36 | 118% |
| Mutant 37 | 122% |

All variants exhibit increased washing performance in comparison with the variant according to SEQ ID NO:16.

The invention claimed is:

1. A protease comprising:
an amino acid sequence having at least 70% sequence identity with the amino acid sequence given in SEQ ID NO: 1 over its entire length and having, in each case based on the numbering according to SEQ ID NO: 1:
an amino acid substitution at the position corresponding to position 271 that is Q271E; and
an amino acid substitution at the position corresponding to position 9 that is P9T, P9H, P9S, or P9A; and
a further amino acid substitution comprising at least:
A48V, G131S, T133R and S224A;
G131D, T133R and S224A;
N130D, G131N, T133K and N144K;
A29G, N130D, G131N and T133R;
N130D, G131S, T133K and S224A;
N130D, G131N, T133K, N144L and N252S;
G131S, N144K and S224T;
N130S, G131S, T133Y, N144L and S224A;
D101E, G131N and S224A;
N130D, N144K and N252T;
N130D, N144K, N252T, and an additional substitution at at least one of the positions corresponding to positions 18, 61, 92, 99, 137, 149, 156, 159, 162, 166, 172, 192, 199, 217, 265, or combinations thereof; or
N130H, G131S and S224A.

2. The protease according to claim 1, wherein:
the further substitution comprises N130D, N144K and N252T and the additional amino acid substitution is selected from the group consisting of 18D, 61Y, 92S, 99Y, 137K, 149I, 156G, 156Y, 159I, 162S, 166M, 172G, 172P, 192V, 199M, 217M, 265A, or combinations thereof in each case based on the numbering according to SEQ ID NO:1.

3. The protease according to claim 1,
wherein the further amino acid substitution comprises another substitution at at least one of the positions corresponding to positions 29, 48, 101, 252, or combinations thereof in each case based on the numbering according to SEQ ID NO: 1.

4. The protease according to claim 1,
wherein the further substitution comprises N130D, N144K and N252T and the additional substitution occurs at at least one of the positions corresponding to positions 99, 137, 149, 156, 162, 166, 172, 192, 199, 217, 224, 265, or combinations thereof.

5. The protease according to claim 1,
wherein the further substitution comprises N130D, N144K and N252T and the additional substitution occurs at at least one of the positions corresponding to positions 18, 61, 92, 159, 162, 192, or combinations thereof.

6. The protease according to claim 5,
wherein the additional substitution occurs at at least two positions corresponding to positions (i) 61 and 92 or (ii) 18 and 159.

7. The protease according to claim 1,
wherein the further substitution comprises N130D, N144K and N252T and the additional substitution occurs at at least the position corresponding to position 172.

8. The protease according to claim 1, wherein the protease has an amino acid sequence according to one of SEQ ID NOs: 3-12 and 16-24.

9. The protease of claim 1, wherein the amino acid sequence has at least 80% sequence identity with the amino acid sequence given in SEQ ID NO: 1 over its entire length.

10. A composition comprising:
at least one protease according to claim 1; wherein the composition is a washing or cleaning composition; and one or more surfactants.

11. The composition of claim 10, wherein the further substitution comprises N130D, N144K and N252T and the additional amino acid substitution is selected from the group consisting of 18D, 61Y, 92S, 99Y, 137K, 149I, 156G, 156Y, 159I, 162S, 166M, 172G, 172P, 192V, 199M, 217M, 265A, or combinations thereof in each case based on the numbering according to SEQ ID NO:1.

12. The composition of claim 10, wherein the further substitution comprises N130D, N144K and N252T and the additional substitution of the protease occurs at at least the position corresponding to position 172.

13. The composition of claim 10, wherein the further substitution comprises N130D, N144K and N252T and the additional substitution of the protease comprises:
S156G;
S156Y;
Y217M;
N137K;
F61Y;
A92S;
F61Y, and A92S;
T162S;
A192V;
A18D, and T159I; or
D172G.

14. A nucleic acid that codes for a protease according to claim 1.

15. A vector containing a nucleic acid according to claim 14.

16. A non-human host cell comprising: a protease according to claim 1.

17. A method for preparing a protease, comprising:
a) cultivating a host cell according to claim 16 in a culture medium; and
b) isolating the protease from the culture medium or from the host cell.

* * * * *

SEQUENCE LISTING

```
<160> NUMBER OF SEQ ID NOS: 25

<210> SEQ ID NO 1
<211> LENGTH: 275
<212> TYPE: PRT
<213> ORGANISM: Bacillus pumilus

<400> SEQUENCE: 1

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Gly Ser Thr Ala Leu Lys Asn Ala Val Asp Thr Ala Asn Asn
    130                 135                 140

Arg Gly Val Val Val Val Ala Ala Ala Gly Asn Ser Gly Ser Thr Gly
```

```
            145                 150                 155                 160
        Ser Thr Ser Thr Val Gly Tyr Pro Ala Lys Tyr Asp Ser Thr Ile Ala
                        165                 170                 175

Val Ala Asn Val Asn Ser Ser Asn Val Arg Asn Ser Ser Ser Ser Ala
                        180                 185                 190

Gly Pro Glu Leu Asp Val Ser Ala Pro Gly Thr Ser Ile Leu Ser Thr
                        195                 200                 205

Val Pro Ser Ser Gly Tyr Thr Ser Tyr Thr Gly Thr Ser Met Ala Ser
                210                 215                 220

Pro His Val Ala Gly Ala Ala Leu Ile Leu Ser Lys Asn Pro Asn
        225                 230                 235                 240

Leu Ser Asn Ser Gln Val Arg Gln Arg Leu Glu Asn Thr Ala Thr Pro
                        245                 250                 255

Leu Gly Asn Ser Phe Tyr Tyr Gly Lys Gly Leu Ile Asn Ala Gln Ala
                        260                 265                 270

Ala Ser Asn
                275

<210> SEQ ID NO 2
<211> LENGTH: 275
<212> TYPE: PRT
<213> ORGANISM: Artificial Sequence
<220> FEATURE:
<223> OTHER INFORMATION: Mutante 2

<400> SEQUENCE: 2

Ala Gln Thr Val Pro Tyr Gly Ile Thr Gln Ile Lys Ala Pro Ala Val
        1               5                   10                  15

His Ala Gln Gly Tyr Lys Gly Ala Asn Val Lys Val Ala Val Leu Asp
                        20                  25                  30

Thr Gly Ile His Ala Ala His Pro Asp Leu Asn Val Ala Gly Gly Ala
                        35                  40                  45

Ser Phe Val Pro Ser Glu Pro Asn Ala Thr Gln Asp Phe Gln Ser His
                        50                  55                  60

Gly Thr His Val Ala Gly Thr Ile Ala Ala Leu Asp Asn Thr Ile Gly
        65                  70                  75                  80

Val Leu Gly Val Ala Pro Ser Ala Ser Leu Tyr Ala Val Lys Val Leu
                        85                  90                  95

Asp Arg Asn Gly Asp Gly Gln Tyr Ser Trp Ile Ile Ser Gly Ile Glu
                        100                 105                 110

Trp Ala Val Ala Asn Asn Met Asp Val Ile Asn Met Ser Leu Gly Gly
                        115                 120                 125

Pro Asn Gly Ser Arg Ala Leu Lys Asn Ala Val Asp Thr Ala Asn Asn
                        130                 135                 140

Arg Gly Val Val Val Ala Ala Gly Asn Ser Gly Ser Thr Gly
        145                 150                 155                 160

Ser Thr Ser Thr Val Gly Tyr Pro Ala Lys Tyr Asp Ser Thr Ile Ala
                        165                 170                 175

Val Ala Asn Val Asn Ser Ser Asn Val Arg Asn Ser Ser Ser Ser Ala
                        180                 185                 190

Gly Pro Glu Leu Asp Val Ser Ala Pro Gly Thr Ser Ile Leu Ser Thr
                        195                 200                 205

Val Pro Ser Ser Gly Tyr Thr Cys Tyr Thr Gly Thr Ser Met Ala Ala
                210                 215                 220

Pro His Val Ala Gly Ala Ala Ala Leu Ile Leu Ser Lys Asn Pro Asn
```

225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 3
<211> LENGTH: 275
<212> TYPE: PRT
<213> ORGANISM: Artificial Sequence
<220> FEATURE:
<223> OTHER INFORMATION: Mutante 3

<400> SEQUENCE: 3

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Val
            35                  40                  45

Ser Phe Val Pro Ser Glu Pro Asn Ala Thr Gln Asp Phe Gln Ser His
        50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asn Ser Ser Arg Ala Leu Lys Asn Ala Val Asp Thr Ala Asn Asn
        130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 4
<211> LENGTH: 275
<212> TYPE: PRT

<213> ORGANISM: Artificial Sequence
<220> FEATURE:
<223> OTHER INFORMATION: Mutante 4

<400> SEQUENCE: 4

```
Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Asp Ser Arg Ala Leu Lys Asn Ala Val Asp Thr Ala Asn Asn
    130                 135                 140

Arg Gly Val Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275
```

<210> SEQ ID NO 5
<211> LENGTH: 275
<212> TYPE: PRT
<213> ORGANISM: Artificial Sequence
<220> FEATURE:
<223> OTHER INFORMATION: Mutante 5

<400> SEQUENCE: 5

```
Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45
```

```
Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asp Asn Ser Lys Ala Leu Lys Asn Ala Val Asp Thr Ala Asn Lys
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Ser
210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
    275

<210> SEQ ID NO 6
<211> LENGTH: 275
<212> TYPE: PRT
<213> ORGANISM: Artificial Sequence
<220> FEATURE:
<223> OTHER INFORMATION: Mutante 6

<400> SEQUENCE: 6

Ala Gln Thr Val Pro Tyr Gly Ile Thr Gln Ile Lys Ala Pro Ala Val
 1               5                  10                  15

His Ala Gln Gly Tyr Lys Gly Ala Asn Val Lys Val Gly Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125
```

```
Pro Asp Asn Ser Arg Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Ser
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275
```

<210> SEQ ID NO 7
<211> LENGTH: 275
<212> TYPE: PRT
<213> ORGANISM: Artificial Sequence
<220> FEATURE:
<223> OTHER INFORMATION: Mutante 7

<400> SEQUENCE: 7

```
Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asp Ser Ser Lys Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
            195                 200                 205
```

```
Val Pro Ser Ser Gly Tyr Thr Cys Tyr Thr Gly Thr Ser Met Ala Ala
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 8
<211> LENGTH: 275
<212> TYPE: PRT
<213> ORGANISM: Artificial Sequence
<220> FEATURE:
<223> OTHER INFORMATION: Mutante 8

<400> SEQUENCE: 8

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asp Asn Ser Lys Ala Leu Lys Asn Ala Val Asp Thr Ala Asn Leu
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
                180                 185                 190

Gly Pro Glu Leu Asp Val Ser Ala Pro Gly Thr Ser Ile Leu Ser Thr
                195                 200                 205

Val Pro Ser Ser Gly Tyr Thr Cys Tyr Thr Gly Thr Ser Met Ala Ser
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Ser Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275
```

<210> SEQ ID NO 9
<211> LENGTH: 275
<212> TYPE: PRT
<213> ORGANISM: Artificial Sequence
<220> FEATURE:
<223> OTHER INFORMATION: Mutante 9

<400> SEQUENCE: 9

```
Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Ser Ser Thr Ala Leu Lys Asn Ala Val Asp Thr Ala Asn Lys
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Thr
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275
```

<210> SEQ ID NO 10
<211> LENGTH: 275
<212> TYPE: PRT
<213> ORGANISM: Artificial Sequence
<220> FEATURE:
<223> OTHER INFORMATION: Mutante 10

<400> SEQUENCE: 10

```
Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30
```

```
Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
 50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
             115                 120                 125

Pro Ser Ser Ser Tyr Ala Leu Lys Asn Ala Val Asp Thr Ala Asn Leu
         130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                 165                 170                 175

Val Ala Asn Val Asn Ser Ser Asn Val Arg Asn Ser Ser Ser Ser Ala
             180                 185                 190

Gly Pro Glu Leu Asp Val Ser Ala Pro Gly Thr Ser Ile Leu Ser Thr
         195                 200                 205

Val Pro Ser Ser Gly Tyr Thr Cys Tyr Thr Gly Thr Ser Met Ala Ala
210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                 245                 250                 255

Leu Gly Asn Ser Phe Tyr Tyr Gly Lys Gly Leu Ile Asn Ala Glu Ala
             260                 265                 270

Ala Ser Asn
        275

<210> SEQ ID NO 11
<211> LENGTH: 275
<212> TYPE: PRT
<213> ORGANISM: Artificial Sequence
<220> FEATURE:
<223> OTHER INFORMATION: Mutante 11

<400> SEQUENCE: 11

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
 50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Glu Gly Gln Tyr Ser Trp Ile Ile Ser Gly Ile Glu
                100                 105                 110
```

```
Trp Ala Val Ala Asn Asn Met Asp Val Ile Asn Met Ser Leu Gly Gly
            115                 120                 125

Pro Asn Asn Ser Thr Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 12
<211> LENGTH: 275
<212> TYPE: PRT
<213> ORGANISM: Artificial Sequence
<220> FEATURE:
<223> OTHER INFORMATION: Mutante 12

<400> SEQUENCE: 12

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
            115                 120                 125

Pro His Ser Ser Thr Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190
```

```
Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Ala
        210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 13
<211> LENGTH: 275
<212> TYPE: PRT
<213> ORGANISM: Artificial Sequence
<220> FEATURE:
<223> OTHER INFORMATION: Mutante 1

<400> SEQUENCE: 13

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Gly Ser Thr Ala Leu Lys Asn Ala Val Asp Thr Ala Asn Asn
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Ser
        210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270
```

```
<210> SEQ ID NO 14
<211> LENGTH: 275
<212> TYPE: PRT
<213> ORGANISM: Artificial Sequence
<220> FEATURE:
<223> OTHER INFORMATION: Mutante 13

<400> SEQUENCE: 14
```

| Ala | Gln | Thr | Val | Pro | Tyr | Gly | Ile | Thr | Gln | Ile | Lys | Ala | Pro | Ala | Val |
|---|---|---|---|---|---|---|---|---|---|---|---|---|---|---|---|
| 1 | | | | 5 | | | | | 10 | | | | | 15 | |

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Gly Ser Thr Ala Leu Lys Asn Ala Val Asp Thr Ala Asn Asn
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

```
<210> SEQ ID NO 15
<211> LENGTH: 275
<212> TYPE: PRT
<213> ORGANISM: Artificial Sequence
<220> FEATURE:
<223> OTHER INFORMATION: Mutante 14

<400> SEQUENCE: 15
```

Ala Gln Thr Val Pro Tyr Gly Ile Pro Gln Ile Lys Ala Pro Ala Val

```
            1               5                  10                 15
         His Ala Gln Gly Tyr Lys Gly Ala Asn Val Lys Val Ala Val Leu Asp
                        20                  25                 30

Thr Gly Ile His Ala Ala His Pro Asp Leu Asn Val Ala Gly Gly Ala
                        35                  40                 45

Ser Phe Val Pro Ser Glu Pro Asn Ala Thr Gln Asp Phe Gln Ser His
             50                  55                  60

Gly Thr His Val Ala Gly Thr Ile Ala Ala Leu Asp Asn Thr Ile Gly
         65                  70                  75                  80

Val Leu Gly Val Ala Pro Ser Ala Ser Leu Tyr Ala Val Lys Val Leu
                         85                  90                  95

Asp Arg Asn Gly Asp Gly Gln Tyr Ser Trp Ile Ile Ser Gly Ile Glu
                         100                 105                110

Trp Ala Val Ala Asn Asn Met Asp Val Ile Asn Met Ser Leu Gly Gly
                         115                 120                125

Pro Asp Gly Ser Thr Ala Leu Lys Asn Ala Val Asp Thr Ala Asn Lys
             130                 135                 140

Arg Gly Val Val Val Ala Ala Ala Gly Asn Ser Gly Ser Thr Gly
         145                 150                 155                160

Ser Thr Ser Thr Val Gly Tyr Pro Ala Lys Tyr Asp Ser Thr Ile Ala
                         165                 170                 175

Val Ala Asn Val Asn Ser Ser Asn Val Arg Asn Ser Ser Ser Ser Ala
                         180                 185                 190

Gly Pro Glu Leu Asp Val Ser Ala Pro Gly Thr Ser Ile Leu Ser Thr
                         195                 200                 205

Val Pro Ser Ser Gly Tyr Thr Ser Tyr Thr Gly Thr Ser Met Ala Ser
             210                 215                 220

Pro His Val Ala Gly Ala Ala Ala Leu Ile Leu Ser Lys Asn Pro Asn
         225                 230                 235                 240

Leu Ser Asn Ser Gln Val Arg Gln Arg Leu Glu Thr Thr Ala Thr Pro
                         245                 250                 255

Leu Gly Asn Ser Phe Tyr Tyr Gly Lys Gly Leu Ile Asn Ala Glu Ala
                         260                 265                 270

Ala Ser Asn
                275

<210> SEQ ID NO 16
<211> LENGTH: 275
<212> TYPE: PRT
<213> ORGANISM: Artificial Sequence
<220> FEATURE:
<223> OTHER INFORMATION: Mutante 15

<400> SEQUENCE: 16

Ala Gln Thr Val Pro Tyr Gly Ile Thr Gln Ile Lys Ala Pro Ala Val
         1               5                   10                  15

His Ala Gln Gly Tyr Lys Gly Ala Asn Val Lys Val Ala Val Leu Asp
                         20                  25                  30

Thr Gly Ile His Ala Ala His Pro Asp Leu Asn Val Ala Gly Gly Ala
                         35                  40                  45

Ser Phe Val Pro Ser Glu Pro Asn Ala Thr Gln Asp Phe Gln Ser His
             50                  55                  60

Gly Thr His Val Ala Gly Thr Ile Ala Ala Leu Asp Asn Thr Ile Gly
         65                  70                  75                  80

Val Leu Gly Val Ala Pro Ser Ala Ser Leu Tyr Ala Val Lys Val Leu
```

```
                    85                  90                  95
Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
                115                 120                 125

Pro Asp Gly Ser Thr Ala Leu Lys Asn Ala Val Asp Thr Ala Asn Lys
            130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 17
<211> LENGTH: 275
<212> TYPE: PRT
<213> ORGANISM: Artificial Sequence
<220> FEATURE:
<223> OTHER INFORMATION: Mutante 16

<400> SEQUENCE: 17

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
        50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
                115                 120                 125

Pro Asp Gly Ser Thr Ala Leu Lys Asn Ala Val Asp Thr Ala Asn Lys
            130                 135                 140

Arg Gly Val Val Val Ala Ala Gly Asn Gly Ser Thr Gly
145                 150                 155                 160

Ser Thr Ser Thr Val Gly Tyr Pro Ala Lys Tyr Asp Ser Thr Ile Ala
```

```
                    165                 170                 175
Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
            245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 18
<211> LENGTH: 275
<212> TYPE: PRT
<213> ORGANISM: Artificial Sequence
<220> FEATURE:
<223> OTHER INFORMATION: Mutante 17

<400> SEQUENCE: 18

Ala Gln Thr Val Pro Tyr Gly Ile Thr Gln Ile Lys Ala Pro Ala Val
1               5                  10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
            115                 120                 125

Pro Asp Gly Ser Thr Ala Leu Lys Asn Ala Val Asp Thr Ala Asn Lys
    130                 135                 140

Arg Gly Val Val Val Ala Ala Ala Gly Asn Tyr Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
```

Leu Gly Asn Ser Phe Tyr Tyr Gly Lys Gly Leu Ile Asn Ala Glu Ala
            260                 265                 270

Ala Ser Asn
        275

<210> SEQ ID NO 19
<211> LENGTH: 275
<212> TYPE: PRT
<213> ORGANISM: Artificial Sequence
<220> FEATURE:
<223> OTHER INFORMATION: Mutante 18

<400> SEQUENCE: 19

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Gly Ser Thr Ala Leu Lys Asn Ala Val Asp Thr Ala Asn Lys
130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Met Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 20
<211> LENGTH: 275
<212> TYPE: PRT
<213> ORGANISM: Artificial Sequence
<220> FEATURE:
<223> OTHER INFORMATION: Mutante 19

-continued

<400> SEQUENCE: 20

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Gly Ser Thr Ala Leu Lys Lys Ala Val Asp Thr Ala Asn Lys
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 21
<211> LENGTH: 275
<212> TYPE: PRT
<213> ORGANISM: Artificial Sequence
<220> FEATURE:
<223> OTHER INFORMATION: Mutante 20

<400> SEQUENCE: 21

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Tyr Gln Ser His
    50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ser Val Lys Val Leu
                 85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Gly Ser Thr Ala Leu Lys Asn Ala Val Asp Thr Ala Asn Lys
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 22
<211> LENGTH: 275
<212> TYPE: PRT
<213> ORGANISM: Artificial Sequence
<220> FEATURE:
<223> OTHER INFORMATION: Mutante 21

<400> SEQUENCE: 22

Ala Gln Thr Val Pro Tyr Gly Ile Pro Gln Ile Lys Ala Pro Ala Val
 1               5                  10                  15

His Ala Gln Gly Tyr Lys Gly Ala Asn Val Lys Val Ala Val Leu Asp
                 20                  25                  30

Thr Gly Ile His Ala Ala His Pro Asp Leu Asn Val Ala Gly Gly Ala
             35                  40                  45

Ser Phe Val Pro Ser Glu Pro Asn Ala Thr Gln Asp Phe Gln Ser His
     50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Gly Ser Thr Ala Leu Lys Asn Ala Val Asp Thr Ala Asn Lys
    130                 135                 140

Arg Gly Val Val Val Ala Ala Ala Gly Asn Ser Gly Ser Thr Gly
145                 150                 155                 160

Ser Ser Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 23
<211> LENGTH: 275
<212> TYPE: PRT
<213> ORGANISM: Artificial Sequence
<220> FEATURE:
<223> OTHER INFORMATION: Mutante 22

<400> SEQUENCE: 23

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Gly Ser Thr Ala Leu Lys Asn Ala Val Asp Thr Ala Asn Lys
130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Val
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

```
Pro His Val Ala Gly Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
            245                 250                 255

Leu Gly Asn Ser Phe Tyr Tyr Gly Lys Gly Leu Ile Asn Ala Glu Ala
            260                 265                 270

Ala Ser Asn
    275

<210> SEQ ID NO 24
<211> LENGTH: 275
<212> TYPE: PRT
<213> ORGANISM: Artificial Sequence
<220> FEATURE:
<223> OTHER INFORMATION: Mutante 23

<400> SEQUENCE: 24

Ala Gln Thr Val Pro Tyr Gly Ile His Gln Ile Lys Ala Pro Ala Val
1               5                   10                  15

His Asp Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Gly Ser Thr Ala Leu Lys Asn Ala Val Asp Thr Ala Asn Lys
130                 135                 140

Arg Gly Val Val Val Ala Ala Ala Gly Asn Ser Gly Ser Ile Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
            245                 250                 255

Leu Gly Asn Ser Phe Tyr Tyr Gly Lys Gly Leu Ile Asn Ala Glu Ala
            260                 265                 270

Ala Ser Asn
    275

<210> SEQ ID NO 25
<211> LENGTH: 275
```

```
<212> TYPE: PRT
<213> ORGANISM: Artificial Sequence
<220> FEATURE:
<223> OTHER INFORMATION: Mutante 24

<400> SEQUENCE: 25

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
            115                 120                 125

Pro Asn Gly Ser Thr Ala Leu Lys Asn Ala Val Asp Thr Ala Asn Asn
130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Gly Ser Thr Ile Ala
            165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
            245                 250                 255

Leu Gly Asn Ser Phe Tyr Tyr Gly Lys Gly Leu Ile Asn Ala Glu Ala
            260                 265                 270

Ala Ser Asn
    275
```